(12) United States Patent
Fernandez De Castro et al.

(10) Patent No.: US 12,332,265 B2
(45) Date of Patent: Jun. 17, 2025

(54) SAMPLE PREPARATION INSTRUMENT

(71) Applicant: Beckman Coulter, Inc., Brea, CA (US)

(72) Inventors: Juan Fernandez De Castro, Miami, FL (US); William Gutierrez, Miami, FL (US); Martin Adelmann, Cologne (DE); Jose Cano, Miami, FL (US); Eric Statler, Coral Gables, FL (US)

(73) Assignee: Beckman Coulter, Inc., Brea, CA (US)

( * ) Notice: Subject to any disclaimer, the term of this patent is extended or adjusted under 35 U.S.C. 154(b) by 1122 days.

(21) Appl. No.: 17/127,439

(22) Filed: Dec. 18, 2020

(65) Prior Publication Data

US 2021/0199682 A1 Jul. 1, 2021

Related U.S. Application Data

(60) Provisional application No. 62/954,299, filed on Dec. 27, 2019.

(51) Int. Cl.
*G01N 35/10* (2006.01)
*G01N 15/01* (2024.01)
(Continued)

(52) U.S. Cl.
CPC ..... *G01N 35/1016* (2013.01); *G01N 15/0656* (2013.01); *G01N 33/56972* (2013.01);
(Continued)

(58) Field of Classification Search
CPC ........ G01N 1/30; G01N 1/31; G01N 15/0656; G01N 15/075; G01N 2001/386;
(Continued)

(56) References Cited

U.S. PATENT DOCUMENTS

| 5,308,772 A | 5/1994 | Sakata et al. |
| 5,631,165 A | 5/1997 | Chupp et al. |

(Continued)

FOREIGN PATENT DOCUMENTS

| CN | 1985168 A | 6/2007 |
| CN | 101315323 A | 12/2008 |

(Continued)

OTHER PUBLICATIONS

Japanese Notice of Rejection in Application 2022-537475, mailed May 22, 2023, 22 pgs.

(Continued)

*Primary Examiner* — Jennifer Wecker
*Assistant Examiner* — Jonathan Bortoli
(74) *Attorney, Agent, or Firm* — Merchant & Gould P.C.

(57) ABSTRACT

A sample preparation instrument with an integrated device for estimating a concentration of white blood cells in a specimen is described. The sample preparation instrument receives a specimen for which a sample is to be prepared for analysis. The integrated device can implement an optical method, an electrical resistance method, or a flow cytometry method, for example, to estimate the white blood cell concentration in the specimen. For some types of analysis, a sample volume of the specimen is dependent on the white blood cell concentration. Therefore, the sample preparation instrument can automatically determine and adjust the sample volume of the specimen based on the estimated white blood cell concentration prior to adding additional reagents, such as labeling reagents and/or lytic reagents, to prepare the sample.

12 Claims, 25 Drawing Sheets

(51) Int. Cl.
    *G01N 15/06* (2024.01)
    *G01N 15/075* (2024.01)
    *G01N 33/569* (2006.01)
    *G06T 7/00* (2017.01)
(52) U.S. Cl.
    CPC ....... *G01N 35/1095* (2013.01); *G06T 7/0012* (2013.01); *G01N 2015/016* (2024.01); *G01N 15/075* (2024.01); *G06T 2207/30024* (2013.01); *G06T 2207/30242* (2013.01)
(58) Field of Classification Search
    CPC ....... G01N 2015/011; G01N 2015/016; G01N 2015/1486; G01N 33/56972; G01N 35/1016; G01N 35/1095; G06T 2207/30024; G06T 2207/30242; G06T 7/0012
    See application file for complete search history.

(56) References Cited

U.S. PATENT DOCUMENTS

| | | | |
|---|---|---|---|
| 5,812,419 A | 9/1998 | Chupp et al. |
| 5,888,752 A | 3/1999 | Malin et al. |
| 5,891,734 A | 4/1999 | Gill et al. |
| 5,939,326 A | 8/1999 | Chupp et al. |
| 6,524,858 B1 | 2/2003 | Zelmanovic et al. |
| 7,618,587 B2 | 11/2009 | Kawate |
| RE42,143 E | 2/2011 | Roche et al. |
| 7,894,047 B2 | 2/2011 | Hamada et al. |
| 7,916,280 B2 | 3/2011 | Ueno et al. |
| 8,273,294 B2 | 9/2012 | Padmanabhan et al. |
| 8,339,585 B2 | 12/2012 | Wells et al. |
| 8,663,559 B2 | 3/2014 | Shibata et al. |
| 8,841,117 B2 | 9/2014 | Nagai et al. |
| 8,920,726 B2 | 12/2014 | Matsumoto et al. |
| 8,968,661 B2 | 3/2015 | Nagai et al. |
| 9,005,916 B2 | 4/2015 | Shibata |
| 9,116,093 B2 | 8/2015 | Abe et al. |
| 9,329,172 B2 | 5/2016 | Kimura et al. |
| 9,453,790 B2 | 9/2016 | Yoshida et al. |
| 9,500,581 B2 | 11/2016 | Yamada et al. |
| 9,541,542 B2 | 1/2017 | Tsuchiya et al. |
| 9,588,102 B2 | 3/2017 | Vidal et al. |
| 9,797,824 B2 | 10/2017 | Wu et al. |
| 9,816,983 B2 | 11/2017 | Fukuma et al. |
| 9,891,210 B2 | 2/2018 | Matsumoto et al. |
| 9,909,973 B2 | 3/2018 | Wanders et al. |
| 9,939,453 B2 | 4/2018 | Lu et al. |
| 10,094,764 B2 | 10/2018 | Winkelman et al. |
| 10,098,581 B2 | 10/2018 | Voldman et al. |
| 10,107,754 B2 | 10/2018 | Suzuki et al. |
| 10,190,961 B2 | 1/2019 | Du et al. |
| 10,215,683 B2 | 2/2019 | Deka |
| 10,220,387 B2 | 3/2019 | Granier et al. |
| 10,241,048 B2 | 3/2019 | Izuka et al. |
| 10,281,382 B2 | 5/2019 | Zahniser et al. |
| 10,281,458 B2 | 5/2019 | Masuda et al. |
| 10,379,120 B2 | 8/2019 | Suzuki et al. |
| 10,422,738 B2 | 9/2019 | Wanders |
| 10,451,638 B2 | 10/2019 | Suzuki et al. |
| 10,481,073 B2 | 11/2019 | Wu et al. |
| 10,605,718 B2 | 3/2020 | Henkel et al. |
| 10,684,207 B2 | 6/2020 | Correia De Matos Nolasco Lamas et al. |
| 2007/0020721 A1 | 1/2007 | Yoshida et al. |
| 2009/0248318 A1 | 10/2009 | Nagai et al. |
| 2010/0054575 A1 | 3/2010 | Zhou et al. |
| 2011/0052037 A1 | 3/2011 | Coumans et al. |
| 2013/0224851 A1 | 8/2013 | Ljungmann et al. |
| 2014/0273060 A1 | 9/2014 | Wu |
| 2014/0273188 A1 | 9/2014 | Mohan et al. |
| 2014/0377771 A1 | 12/2014 | Bibette et al. |
| 2015/0212070 A1* | 7/2015 | Lin ................... B01L 3/502715 422/504 |
| 2016/0061821 A1 | 3/2016 | Tateyama et al. |
| 2017/0276591 A1* | 9/2017 | Krockenberger .. G01N 15/1404 |
| 2018/0024122 A1 | 1/2018 | Wang et al. |
| 2018/0052094 A1 | 2/2018 | Magnin et al. |
| 2018/0128728 A1 | 5/2018 | Lee |
| 2019/0101486 A1 | 4/2019 | Deka |
| 2019/0128793 A1 | 5/2019 | Shirai et al. |
| 2019/0137380 A1 | 5/2019 | Brown et al. |
| 2019/0143330 A1* | 5/2019 | Kanda ................ G01N 15/1459 435/287.3 |
| 2019/0162666 A1 | 5/2019 | Akasaka |
| 2019/0232296 A1 | 8/2019 | Kotake et al. |
| 2020/0096530 A1 | 3/2020 | Selin et al. |
| 2020/0158615 A1 | 5/2020 | Shi et al. |

FOREIGN PATENT DOCUMENTS

| | | |
|---|---|---|
| CN | 101379387 A | 3/2009 |
| CN | 102177427 A | 9/2011 |
| CN | 102636635 A | 8/2012 |
| CN | 102879319 A | 1/2013 |
| CN | 103278439 A | 9/2013 |
| CN | 103439523 A | 12/2013 |
| CN | 104949944 A | 9/2015 |
| CN | 105866012 A | 8/2016 |
| CN | 206095892 U | 4/2017 |
| CN | 107589060 A | 1/2018 |
| CN | 107817208 A | 3/2018 |
| CN | 104344864 B | 8/2018 |
| CN | 108627449 A | 10/2018 |
| CN | 108663303 A | 10/2018 |
| CN | 105136795 B | 12/2018 |
| CN | 109952106 A | 6/2019 |
| CN | 107702967 B | 11/2019 |
| DE | 3503475 A1 | 8/1985 |
| EP | 0 525 398 B1 | 6/1996 |
| EP | 0 810 026 B1 | 10/2003 |
| EP | 1 131 629 B1 | 1/2009 |
| EP | 2 105 723 A2 | 9/2009 |
| EP | 1 887 357 B1 | 5/2013 |
| EP | 2 902 769 A2 | 8/2015 |
| EP | 2 587 262 B1 | 9/2015 |
| EP | 2956759 B1 | 12/2015 |
| EP | 2 703 813 B1 | 5/2017 |
| EP | 3 258 274 A1 | 12/2017 |
| EP | 2 182 370 B1 | 3/2019 |
| EP | 3 452 825 | 3/2019 |
| EP | 2 939 001 B1 | 12/2019 |
| EP | 1 840 571 B1 | 2/2020 |
| EP | 3 001 174 B1 | 3/2020 |
| EP | 3 299 812 B1 | 3/2020 |
| EP | 3 076 157 B1 | 4/2020 |
| EP | 3 239 717 B1 | 5/2020 |
| IN | 337696 B | 12/2010 |
| IN | 299272 B | 11/2011 |
| IN | 330115 B | 2/2014 |
| IN | 201817019804 A | 9/2018 |
| IN | 201838027799 A | 3/2019 |
| IN | 201917022665 A | 7/2019 |
| JP | 09072842 A | 3/1997 |
| JP | 2005534895 A | 11/2005 |
| JP | 2006162524 A | 6/2006 |
| JP | 2007047154 A | 2/2007 |
| JP | 2009008525 A | 1/2009 |
| JP | 2009-243976 A | 10/2009 |
| JP | 2010-85181 A | 4/2010 |
| JP | WO2011089966 A1 | 10/2015 |
| JP | 2016128821 A | 7/2016 |
| JP | 2017075958 A | 4/2017 |
| JP | 2018-205274 A | 12/2018 |
| JP | 2018205046 A | 12/2018 |
| JP | 6461494 B2 | 1/2019 |
| JP | 2019051374 A | 1/2019 |
| JP | 2019-35620 A | 3/2019 |
| JP | 2020-51872 A | 4/2020 |
| WO | 03/040064 A2 | 5/2003 |
| WO | 2014127372 A2 | 8/2014 |
| WO | 2017/087707 A1 | 5/2017 |
| WO | 2017/192739 A1 | 11/2017 |

(56) References Cited

FOREIGN PATENT DOCUMENTS

| | | |
|---|---|---|
| WO | 2018/112145 A1 | 6/2018 |
| WO | 2019/000324 A1 | 1/2019 |
| WO | 2019/168835 A1 | 9/2019 |
| WO | 2019/170993 A1 | 9/2019 |
| WO | 2019/206310 A1 | 10/2019 |
| WO | 2019/206313 A1 | 10/2019 |
| WO | 2020/107496 A1 | 6/2020 |
| WO | 2020/113527 A1 | 6/2020 |

OTHER PUBLICATIONS

Extended European Search Report for Application No. 20215641.0 mailed Apr. 7, 2021.
European Patent Office, Communication pursuant to Article 94(3) EPC mailed Feb. 1, 2023, 4 pages.
International Search Report and Written Opinion for Application No. PCT/US2020/066131 mailed Apr. 7, 2021.
Extended European Search Report for Application No. 24173693.3 mailed Aug. 8, 2024.

\* cited by examiner

SAMPLE PREPARATION INSTRUMENT

CROSS REFERENCE TO RELATED APPLICATION(S)

This application claims the benefit of and priority to U.S. Provisional Patent Application No. 62/954,299, filed on Dec. 27, 2019, entitled SAMPLE PREPARATION INSTRUMENT, the disclosure of which is hereby incorporated by reference in its entirety.

BACKGROUND

To prepare a specimen for analysis by an instrument, such as a flow cytometer or other sample analysis instrument, a sample of the specimen is stained with a labeling reagent that targets a constituent within the sample to facilitate analysis of the targeted constituent. As one example, the target can be a subset of white blood cells in a blood specimen, and the labeling reagent is an antibody that attaches to the subset of white blood cells. Staining of the specimen with the labeling reagent is performed based on a certain number of white blood cells present in the specimen. For example, a particular volume of labeling reagent for staining is used if there is a normal white blood cell concentration of about 4,000 to about 10,000 cells per microliter ($\mu L$) in the specimen. However, if the white blood cell concentration in the specimen is abnormally high or low, the particular volume of labeling reagent will not be effective in targeting the white blood cells or will interfere with the analysis, respectively. Therefore, it is desirable for a white blood cell concentration in the specimen to be obtained before the sample is prepared for the analysis to confirm whether the white blood cell concentration is within an appropriate range for the particular volume of labeling reagent.

SUMMARY

In general terms, this disclosure is directed to a sample preparation instrument, and a method performed by the sample preparation instrument to prepare a sample of a specimen for analysis. In one possible configuration and by non-limiting example, a white blood cell concentration in the specimen is estimated, a volume of the sample to be prepared is determined based on the white blood cell concentration, and one or more reagents, including reagents that target a constituent of the specimen for analysis, are added to the sample to prepare the sample. Various aspects are described in this disclosure, which include, but are not limited to, the following aspects.

One aspect is a sample preparation instrument. The sample preparation instrument can include an input station that receives a specimen, a cell concentration estimator that estimates a concentration of white blood cells in the specimen, and a transfer station that dispenses a sample of the specimen, where a volume of the sample is based on the estimated concentration of white blood cells in the specimen. The sample preparation instrument can also include a reagent station and a lysing station. The reagent station includes a labeling reagent that is added to the sample. The lysing station includes a lytic reagent that is added to the sample. The sample preparation instrument can further include an output station that provides the sample following the addition of the labeling reagent and the lytic reagent to the sample.

Another aspect is a method that includes receiving a specimen as input, estimating a concentration of white blood cells in the specimen, and dispensing a sample of the specimen, where a volume of the sample is based on the estimated concentration of white blood cells in the specimen. The method also includes adding one or more labeling reagents to the sample, adding one or more lytic reagents to the sample, and providing the sample of the specimen as output following the addition of the one or more labeling reagents and the one or more lytic reagents to the sample.

A further aspect is a sample preparation and analysis instrument that includes an input station that receives a specimen, a cell concentration estimator that estimates a concentration of white blood cells in the specimen, and a transfer station that dispenses a sample of the specimen, where a volume of the sample is based on the estimated concentration of white blood cells in the specimen. The sample preparation and analysis instrument also includes a reagent station and a lysing station. The reagent station includes a labeling reagent that is added to the sample. The lysing station includes a lytic reagent that is added to the sample. The sample preparation and analysis instrument further includes a sample analyzer that performs an analysis on the sample following the addition of the one or more labeling reagents and the one or more lytic reagents to the sample, and an output station providing results of the analysis.

DETAILED DESCRIPTION

Figure 1:
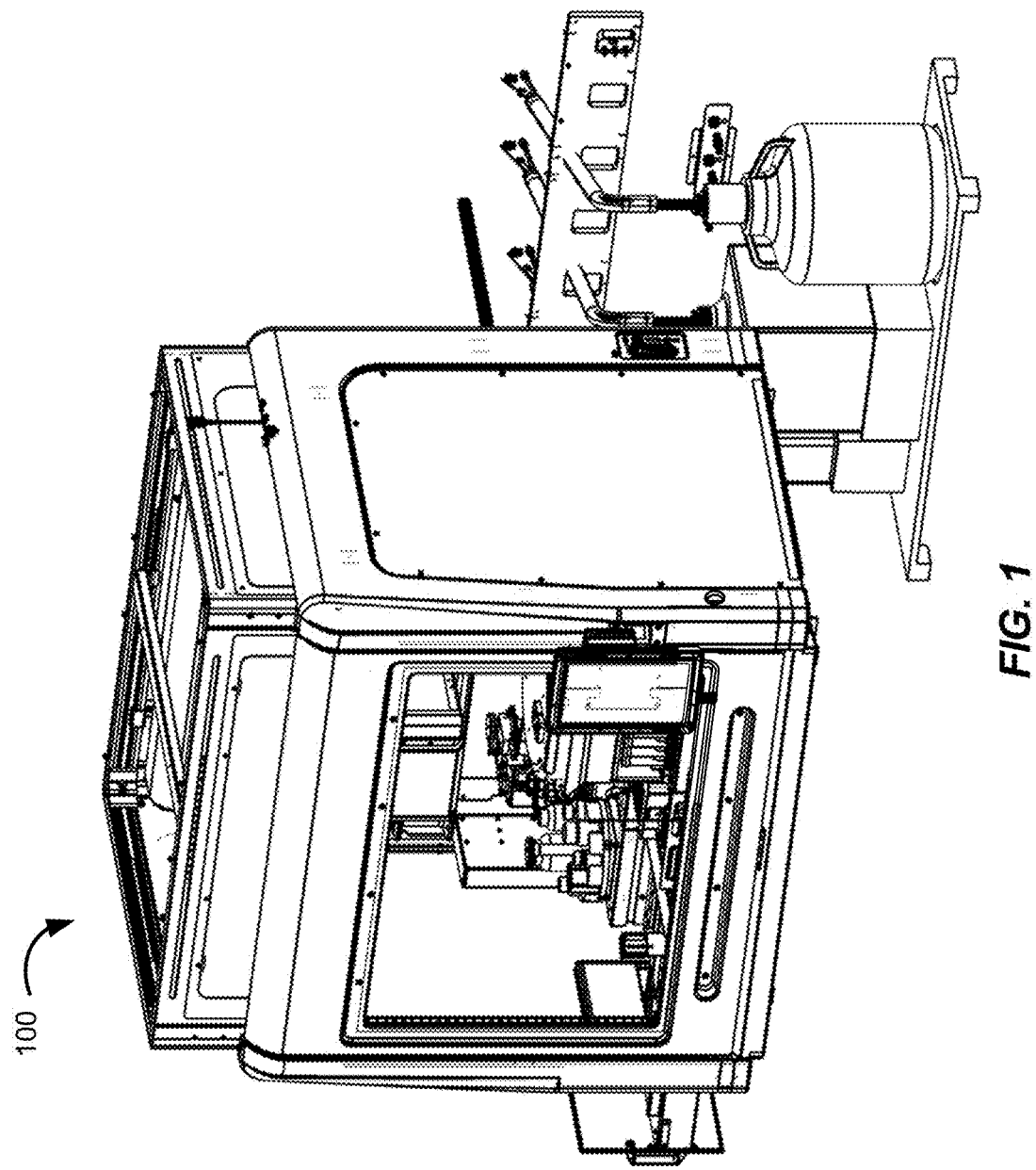
FIG. 1 depicts an example sample preparation instrument.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 depicts an example sample preparation instrument 100. The sample preparation instrument 100 can be used to prepare a sample of a specimen for subsequent analysis, such as for a flow cytometry panel. Example specimens can include whole blood, bone marrow, dissociated tissues, peripheral mononuclear cells, fine needle aspirates, cerebrospinal fluid, and other single cell-suspensions. As one example, a laboratory providing flow cytometry services receives a whole blood specimen to be prepared for a leukemia or lymphoma panel. Constituents of blood include plasma, red blood cells, white blood cells, and platelets. Leukemia or lymphoma affect white blood cells (e.g., cause abnormally high white blood cell counts), and therefore subsets of the white blood cells are the constituent of the blood that is targeted for analysis in the leukemia or lymphoma panel. To prepare a sample of the blood for the panel, a labeling reagent, such as an antibody reagent that attaches to white blood cells, is used to stain the blood. For example, about 100 μL of blood is stained with about 20 μL of the antibody reagent and incubated for about 10 to 20 minutes. The antibody reagent can include a fluorescent dye, for example, that allows for analysis of the white blood cells by flow cytometry. In some examples, cell washing is performed on the blood prior to adding the antibody reagent in order to remove the plasma and associated proteins that interfere with staining (e.g., such that primarily red blood cells and white blood cells remain). A lytic reagent is then added to the sample and incubated to destroy the red blood cells. In some examples, another wash can be performed to slow the lytic activity to avoid destruction of the white blood cells and/or to remove red blood cell debris. The sample can then be analyzed. For example, the leukemia or lymphoma panel can be performed by a flow cytometer.

The volume of the antibody reagent added to the blood is based on the white blood cell concentration in the blood. For example, 20 μL of the antibody reagent is added for a normal white blood cell concentration of about 4,000 cells/μL to about 10,000 cells/μL in the blood. However, if the patient has leukemia causing an abnormally high white blood cell concentration of 50,000 cells/μL, the 20 μL of the antibody reagent won't be effective in targeting the white blood cells because it was titrated or dosed for a lower, normal range of white blood cell concentration. To account for this, the same volume of reagent can be added to a lesser volume of blood comprising a lower number of white blood cells. For example, instead of staining about 100 μL blood with about 20 μL of the antibody, only 50 μL of blood is stained with about 20 μL of the antibody reagent. Conversely, if the patient has an abnormally low white blood cell concentration of about 1,000 cells/μL, the antibody reagent will be in excess and interfere with the analysis because it was titrated or dosed for a higher, normal range of white blood cell concentration. To account for this, the same volume of reagent can be added to a greater volume of blood comprising a higher number of white blood cells. Accordingly, it is important that at least an estimate of a white blood cell concentration in the specimen is obtained before a sample is prepared for analysis to confirm whether the white blood cell concentration is within an appropriate range for the volume of antibody reagent, and if not, adjust a volume of blood added to the antibody reagent during preparation.

Currently, to obtain the white blood cell concentration, the specimen is first sent to another laboratory, such as a hematology laboratory, prior to preparing the sample for the flow cytometry panel. Depending on how busy the hematology laboratory is and/or the method by which the hematology laboratory provides results, it can take hours to receive the concentration value. Alternatively, the concentration determination can be kept in-house if the laboratory has a separate hematology analyzer, or uses microscopy techniques to determine the concentration. However, having a separate hematology analyzer can be costly as it is one more instrument to be maintained that takes up valuable bench space, and using microscopy is time consuming and labor-intensive. Additionally, in each of the above-described methods, manual adjustment of a volume of specimen for sample preparation is required based on the obtained white blood cell concentration, which is time-consuming and prone to errors.

Aspects of this disclosure provide a more streamlined sample preparation process to overcome the above-discussed disadvantages of current systems and methods. For example, the sample preparation instrument 100 described in detail in the following figures includes a cell concentration estimator integrated therein that estimates a white blood cell concentration in a specimen received for preparation. A volume of a sample of the specimen to be prepared (e.g., also referred to as the "sample volume of the specimen") is determined based on the estimated white blood cell concentration. A sample is then automatically prepared or processed that comprises the determined sample volume of the specimen and one or more other reagents, such as labeling reagents, lytic reagents, and/or buffers. By integrating the cell concentration estimator within the sample preparation instrument 100, the white blood cell concentration estimate is performed timely and without the need to maintain and make space for an additional instrument. Additionally, the sample volume of the specimen is adjusted automatically within the sample preparation instrument 100, avoiding unnecessary errors caused by manual adjustment.

Figure 2:
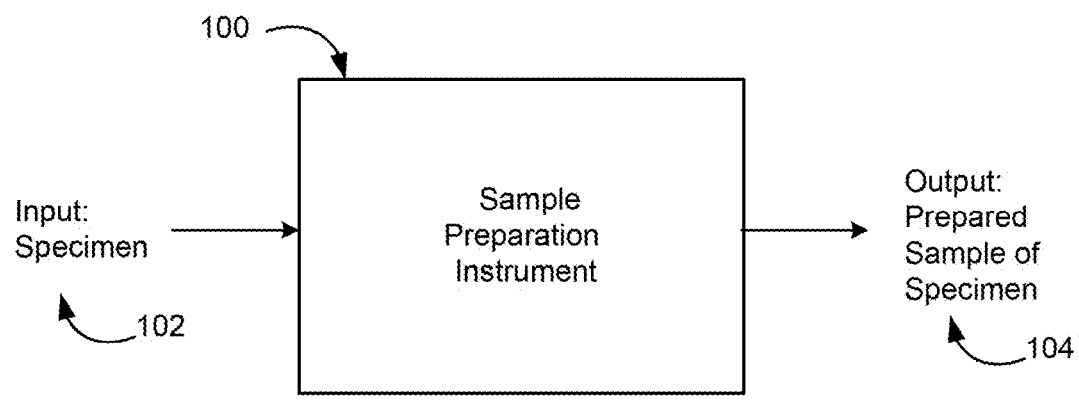
FIG. 2 is a block diagram of the example sample preparation instrument.

FIG. 2 is a block diagram of the example sample preparation instrument 100. The sample preparation instrument 100 receives a specimen, of which a sample is to be prepared for analysis, as input 102. In some examples, the analysis targets specific constituents of the specimen. The sample preparation instrument 100 can estimate a concentration of the targeted constituents in the specimen and prepare a sample accordingly to provide a prepared sample as output 104. For example, a sample volume of the specimen can be determined based on the estimated concentration and a set of predefined rules associated with a type of the analysis the specimen is being prepared for. Reagents can then be added to the sample volume of the specimen, where the reagents can include labeling reagents to target the constituents of the specimen for analysis and lysing reagents to remove interfering constituents of the specimen, for example.

Figure 3:
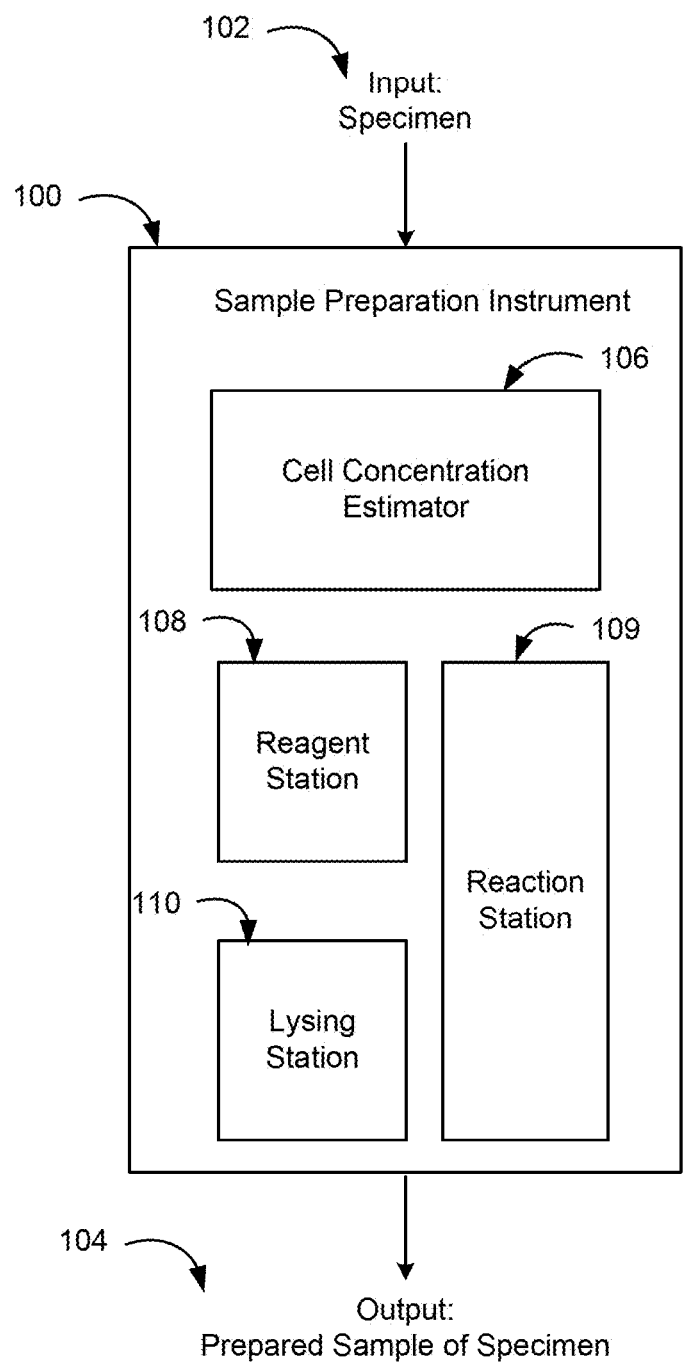
FIG. 3 is a block diagram of basic hardware components of the example sample preparation instrument.

FIG. 3 is a block diagram of basic hardware components of the example sample preparation instrument 100. The sample preparation instrument 100 includes at least a cell concentration estimator 106, a reagent station 108, a reaction station 109, and a lysing station 110.

The sample preparation instrument 100 receives the specimen to be prepared for analysis as the input 102. As one example, the specimen is whole blood to be prepared for a leukemia or lymphoma panel performed by a flow cytometer. The leukemia or lymphoma panel can be performed to analyze subsets of white blood cells in the blood (e.g., the subsets of the white blood cells can be the targeted constituents). The cell concentration estimator 106 is a device or apparatus that can receive an aliquot of the specimen and estimate a white blood cell concentration in the specimen based on an estimated white blood cell concentration in the aliquot. The cell concentration estimator 106 can employ one or more of an optical method, an electrical resistance method, a flow cytometry method, and other similar methods known to one of ordinary skill in the art for estimating white blood cell concentration. A configuration of the cell concentration estimator 106 can be dependent on a type of method employed. Based on the estimated white blood cell concentration in the specimen, a sample volume of the specimen (e.g., a volume of the specimen to be included in the sample prepared for analysis) is determined.

The reagent station 108, described in greater detail with reference to FIG. 4 below, can include a plurality of labeling reagents, where one or more of the labeling reagents are added to the determined sample volume of the specimen. The one or more labeling reagents added can target particular constituents within the sample volume of the specimen. For example, continuing the above example, the reagents can be antibody reagents having fluorescent dyes that attach to the subsets of white blood cells to allow for analysis of the subsets of white bloods cells by the flow cytometer when performing the leukemia or lymphoma panel.

In some examples, the labeling reagents and the sample volume of the specimen come into contact at the reaction station 109. For example, the labeling reagents can be added to the sample volume of the specimen within a well of a reaction plate located within the reaction station 109. As described in greater detail with reference to FIG. 4 below, the reaction station 109 can also include a plate mixer that holds the reaction plate. In some examples, the reaction station 109 is a separate component of the sample preparation instrument 100. In other examples, the reaction station 109 can be integrated with the reagent station 108.

The lysing station 110, described in greater detail with reference to FIG. 4 below, can include a plurality of lytic reagents, where one or more of the lytic reagents are added to the determined sample volume of the specimen. In some examples, the lytic reagents added can destroy red blood cells to prevent the red blood cells from interfering with the analysis. Similar to the labeling reagents, the lytic reagents and the sample volume of the specimen can come into contact at the reaction station 109. For example, the labeling reagents can be added to the sample volume of the specimen within the well of the reaction plate located within the reaction station 109.

Figure 6:
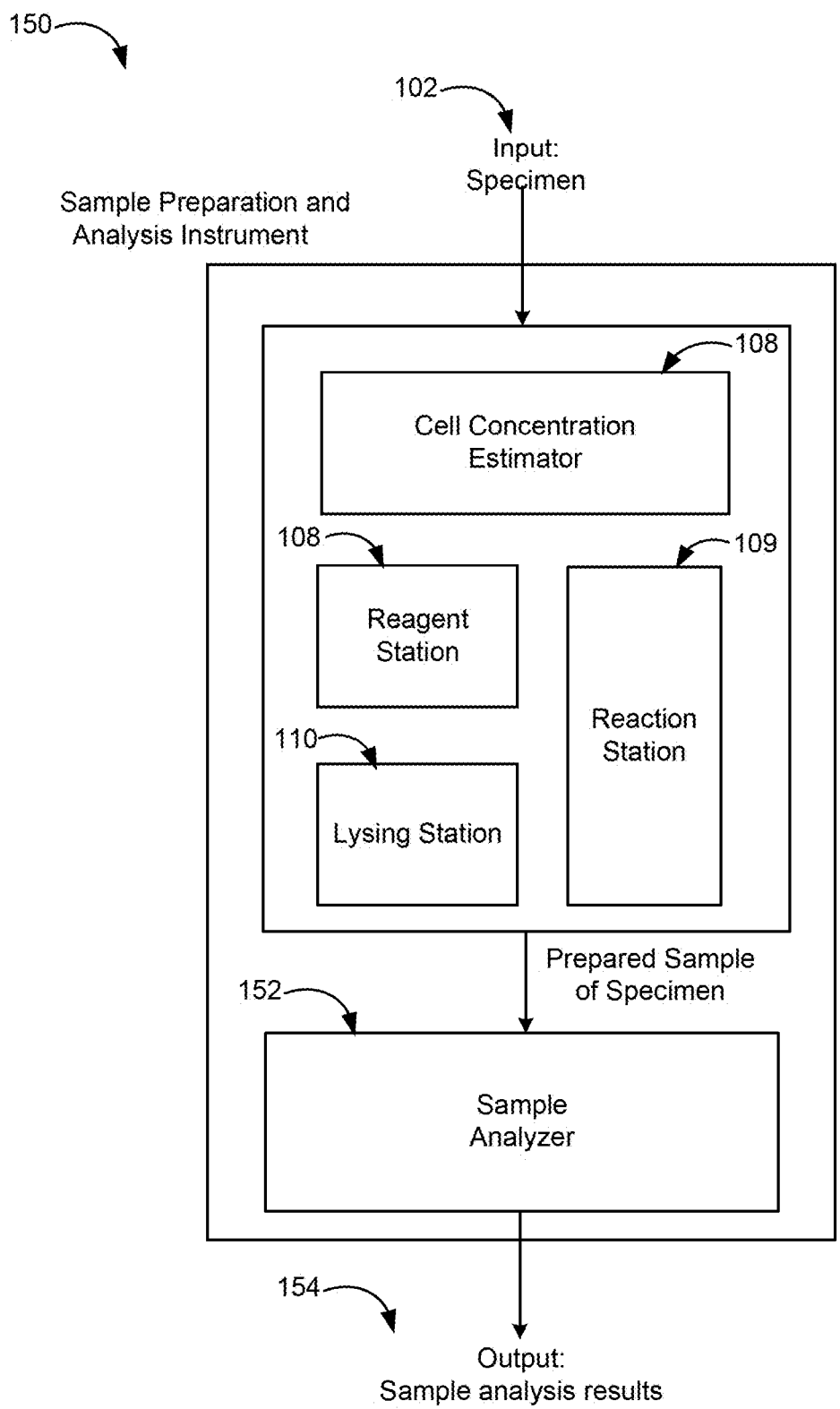
FIG. 6 is a block diagram of basic hardware components of an example sample preparation and analysis instrument.

Following addition of the labeling reagents and lytic reagents, a sample comprising the sample volume of the specimen with the added labeling reagents and lytic reagents is provided as the output 104 of the sample preparation instrument 100. The sample can then be analyzed by a sample analyzer, such as a flow cytometer. In some examples, the sample analyzer is a separate component. In other examples, the sample analyzer can be integrated with the sample preparation instrument, as shown in FIG. 6.

Figure 4:
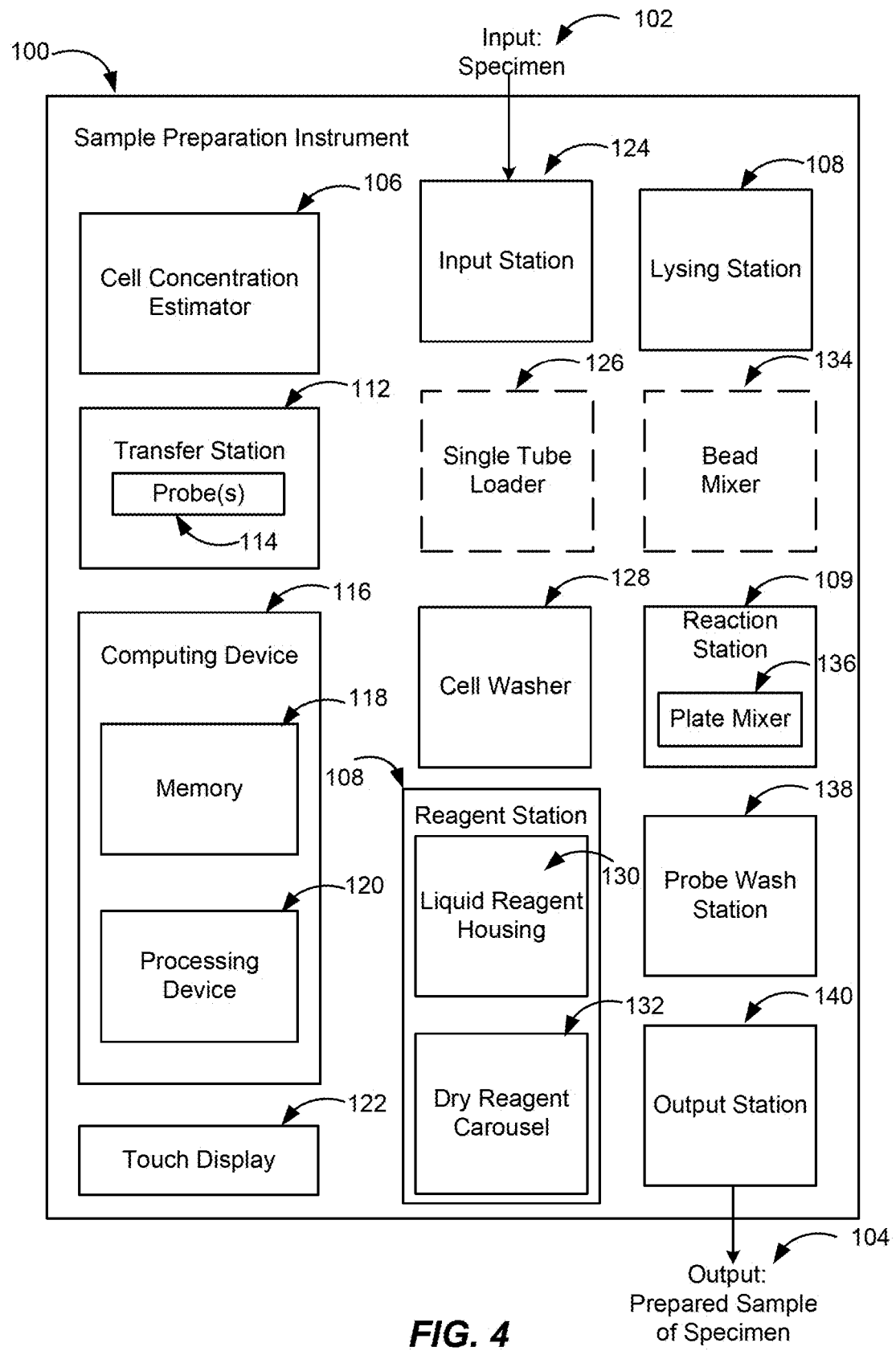
FIG. 4 is a block diagram of additional hardware components of the example sample preparation instrument.
Figure 5:
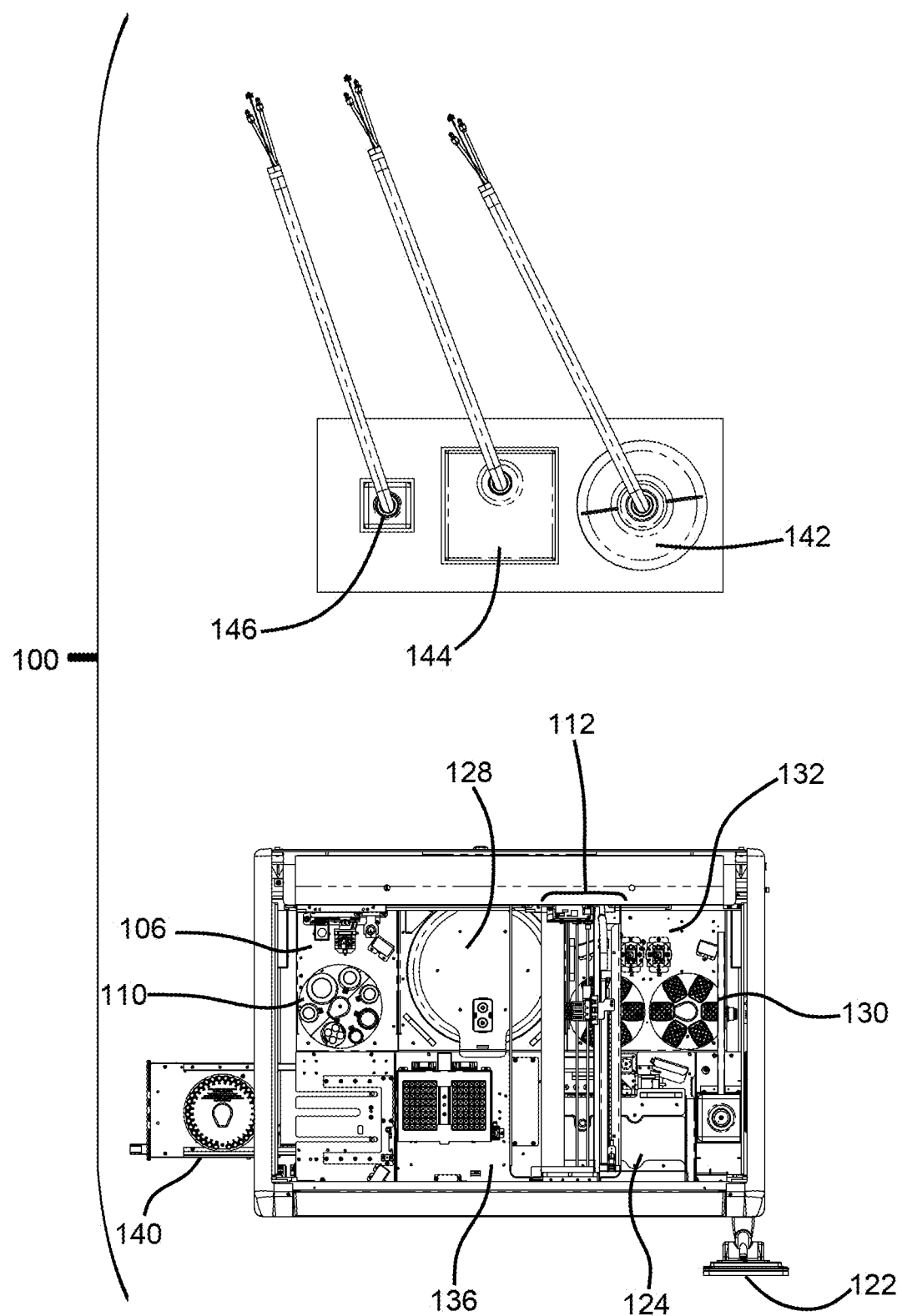
FIG. 5 depicts the hardware components of the example sample preparation instrument described in FIG. 3 and FIG. 4.

FIG. 4 is a block diagram of additional hardware components of the example sample preparation instrument 100, and FIG. 5 depicts these hardware components. In addition to the cell concentration estimator 106, the reagent station 108, the reaction station 109, and the lysing station 110 described in FIG. 3, the sample preparation instrument 100 can further include a transfer station 112 comprising one or more probes 114, a computing device 116 comprising a memory 118 and at least one processing device 120, a touch display 122, an input station 124, a single tube loader 126, a cell washer 128, a liquid reagent housing 130 and a dry reagent carousel 132 within the reagent station 108, a bead mixer 134, a plate mixer 136 within the reaction station 109, a probe wash station 138, and an output station 140.

The probes 114 of the transfer station 112 can aspirate, transport, and dispense various substances among components of the sample preparation instrument 100. The substances can include specimens, labeling reagents, lytic reagents, diluent reagents, and buffers, among other examples. The probes 114 can pierce capped or sealed tubes, vials, cartridges, bottles, or other similar containers to aspirate the substances within or can be inserted into open-top tubes, vials, cartridges, bottles, or other similar open-top containers.

Figure 7:
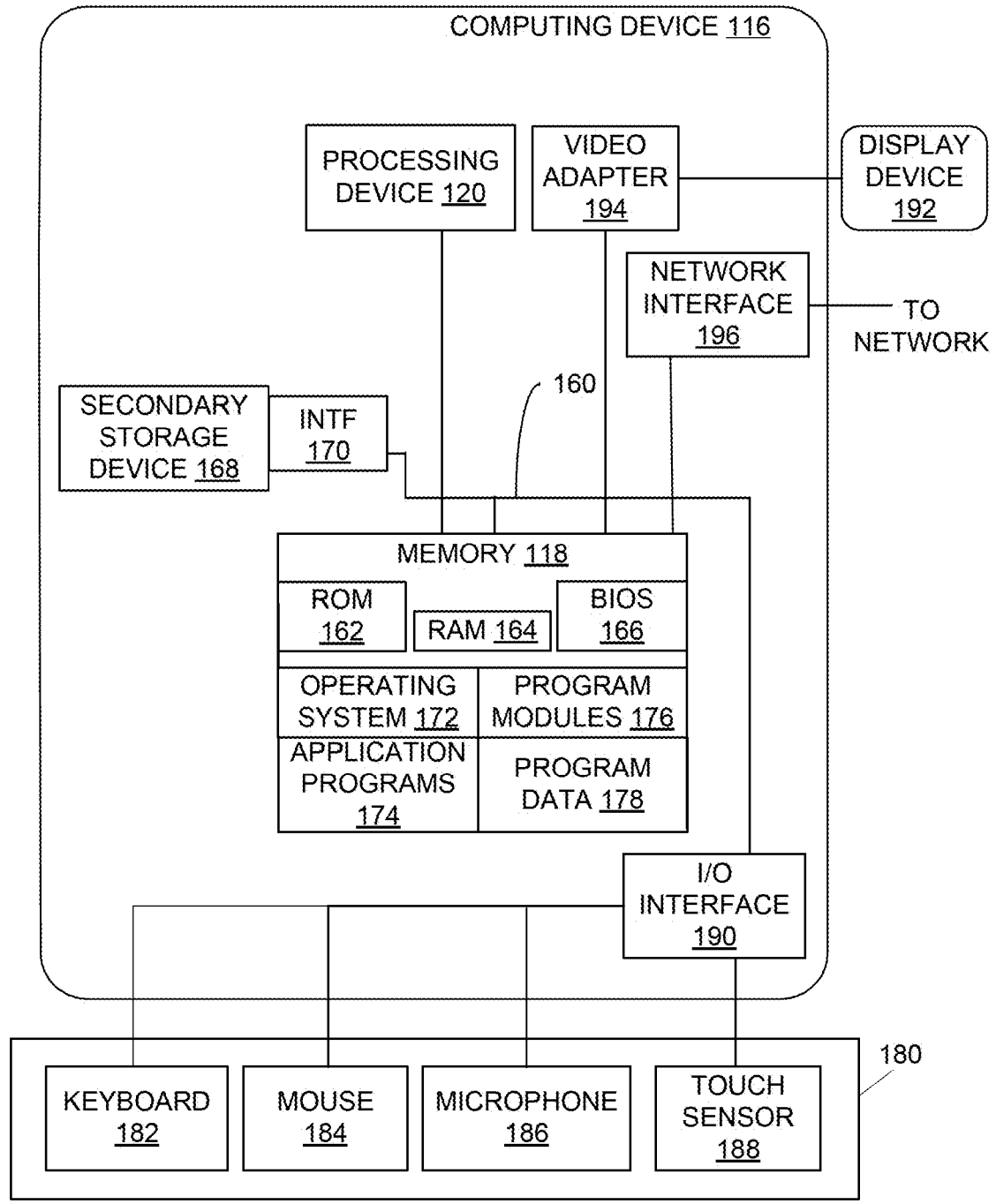
FIG. 7 is an example computing device.

The computing device 116, described in greater detail in FIG. 7, is a controller of the sample preparation instrument 100, as well as an information processor. In some examples, the computing device 116 can store previously authored panels received from a remote computing device. For example, a user, such as a laboratory technician or analyst, can utilize a panel authoring and management application executing on the remote computing device to author panels for different types of specimens and different types of analysis for execution by the sample preparation instrument 100. The authored panels can then be transmitted to the sample preparation instrument 100 over a network or wired connection or a physical memory device such as a USB drive. In other examples, the computing device 116 can execute a panel authoring and management application to allow the user to author the panel using the sample preparation instrument 100 (e.g., via user interfaces provided via the touch display 122), where the authored panels are subsequently stored by the computing device 116. Each panel can define a particular workflow to be performed when preparing a sample of a specimen for the panel. For example, the panel can include a set of rules defining the particular workflow associated with sample preparation, hereinafter referred to as the set of predefined rules.

The computing device 116 can provide the authored panels for display through a specimen loading user interface shown and described with reference to FIG. 13 to enable a user to select one or more of the panels to pair with a received specimen. In some examples, the specimen loading user interface can be provided through the touch display 122 of the sample preparation instrument 100. The selected one or more panels can then be used to manage the operations of the sample preparation instrument 100 while preparing the sample. For example, the set of predefined rules associated with each panel can provide an order of operations, a type and a volume amount of specimen and reagent involved in each operation, a time associated with each operation, and components of the sample preparation instrument 100 involved in each operation, among other examples. Based on the selected one or more panels, the computing device 116 can generate signals for transmission to respective components of the sample preparation instrument 100 that provide instructions for executing the operations.

Additionally, the computing device 116 can operate in conjunction with the cell concentration estimator 106 to determine the white blood cell concentration in the specimen. Based on the set of predefined rules associated with the one or more selected panels, the computing device 116 can further determine whether or not to process the specimen, a sample volume of the specimen based on the white blood cell concentration estimate, and whether the specimen is to be diluted, among other determinations discussed herein.

The touch display 122 provides a user interface that enables the user to interact with the sample preparation instrument 100. For example, one example user interface is the above-described specimen loading user interface, through which the user can select one or more panels for which a sample volume of the specimen is to be prepared. An example user interface for selecting the panel is shown and described in greater detail in reference to FIG. 13. In some examples, once a white blood cell concentration in the specimen is estimated, the user interface can display a range in which the estimated white blood cell concentration falls, as well as a determined sample volume of the specimen that will be prepared by the sample preparation instrument 100 based on the estimated white blood cell concentration. Additionally, as the sample preparation instrument 100 is processing the sample, the touch display 122 can display a status of sample preparation instrument 100 components, including an amount of reagents or other similar solutions remaining, and if any errors occur throughout the sample preparation process. In some examples, the user interface is associated with the panel authoring and management application executing on the computing device 116.

In some examples, the input station 124 receives an input cassette that has been inserted into the sample preparation instrument 100 by a user. An input cassette can hold one or more capped tubes comprising specimen. In some examples, each tube comprises a different specimen (e.g., a specimen from a different patient). The input station 124 is capable of receiving various types of cassettes corresponding to various types of tubes. The input station 124 includes a reader or scanner capable of reading machine-readable codes, such as a barcode, a QR code, or a Radio Frequency Identification (RFID) tag, among other similar examples. In some examples, each tube has an associated code to identify the specimen within the tube that is scanned by the reader or scanner.

The input station 124 can include a rocking mechanism to rock the input cassette in order to maintain specimen homogeneity prior to preparation. The input station 124 can further include a magnet-based mechanism to move the input cassette to a particular position such that the probe 114 of the transfer station 112 is able to pierce a given capped tube held by the input cassette to aspirate specimen from the tube. Once a sample of each specimen within the tubes of the input cassette has been processed or has otherwise been designated not to be processed, the input station 124 can provide the input cassette as an output cassette for removal from the sample preparation instrument by the user. In some examples, an opening on a front panel of the sample preparation instrument 100 provides continuous access to the input station 124. For example, the user can insert new input cassettes or and remove output cassettes at any time via the opening, even when the sample preparation instrument 100 is operating.

Optionally, the sample preparation instrument 100 also includes the single tube loader 126. The single tube loader 126 can be a component of the input station 124 or a separate component. The single tube loader 126 enables insertion of an open-top tube into the sample preparation instrument 100 and positioning such that the probe 114 of the transfer station 112 is able to aspirate a sample of specimen from the tube. In some examples, the open-top tube is utilized when pre-processing is manually performed by the user prior to insertion into the sample preparation instrument 100. Due to the tube having an open top, the single tube loader does not rock the tube to avoid the specimen from spilling. Similar to the capped tubes, the open-top tubes can also include a machine-readable code that is read or scanned to obtain a specimen identifier that identifies the specimen. Alternatively, the specimen identifier can be entered manually when utilizing the single tube loader 126. In further examples, the open-top tubes can be received by the input station 124 in an input cassette designed specifically for open-top tubes, where machine-readable code on the cassette would instruct the input station 124 to disengage the rocking mechanism to prevent the input cassette comprising the open-top tubes from being rocked.

Based on the specimen identifier, the computing device 116 can retrieve the set of predefined rules for the type of analysis. For example, the set of predefined rules can include whether or not a white blood cell concentration in the specimen is to be estimated by the sample preparation instrument 100. If the white blood cell concentration in the specimen is to be estimated by the sample preparation instrument 100, then the probe 114 of the transfer station 112 can transfer an aliquot of the specimen from the tube in the input station 124 or the single tube loader 126 to the cell concentration estimator 106. The cell concentration estimator 106 in conjunction with the computing device 116 can estimate a white blood cell concentration in the specimen by employing one or more of an optical method, an electrical resistance method, a flow cytometry method, and other similar methods known to one of ordinary skill in the art for estimating white blood cell concentration. The aliquot from which the white blood cell concentration is estimated can then be discarded as waste.

Based on the estimated white blood cell concentration in the specimen and the set of predefined rules, the computing device 116 can determine a sample volume of the specimen to be prepared. For example, the set of predefined rules can also include a minimum white blood cell concentration, a maximum white blood cell concentration, and a sample volume of the specimen corresponding to each of one or more ranges of white blood cell concentrations that fall between the minimum and maximum concentrations. Therefore, the computing device 116 can determine the sample volume of the specimen corresponding to the range in which the estimated white blood cell concentration falls, and generate a signal for transmission to a probe 114 of the transfer station 112. Based on the signal, the probe 114 can transfer the determined sample volume of the specimen from the tube at the input station 124 or single tube loader 126 and dispense into a well of a reaction plate, or other similar container. In some examples, the reaction plate is a 48 well plate, where each of the wells is able to hold about 5 milliliters (mL). In some examples, the reaction plate or other similar container can be within the reaction station 109. In other examples, the reaction plate or other similar container is within the reagent station 108.

Optionally, the probe 114 can first transfer the determined sample volume of the specimen to the cell washer 128 to wash the sample volume of the specimen prior to dispensing into a well of the reaction plate or other similar container. In yet other examples, a larger volume of the specimen is washed prior to the determination of the sample volume, and upon determination, the probe 114 can then transfer the determined sample volume of the washed specimen from the cell washer 128 to the well of the reaction plate. For example, when the specimen is whole blood, the blood may contain red blood cells, white blood cells, platelets, plasma and associated proteins. The cell washer 128 can perform cell washing to remove the plasma and associated proteins. The cell washer 128 can include a vessel holding the sample volume of the specimen and an actuating device capable of causing the vessel to spin about an axis. In some examples, the vessel includes a body defining a cavity and a pocket, where the pocket extends radially outward relative to an inner wall surface defining the cavity. As a result of this configuration, as the vessel is being spun about its axis, the heavier blood cells in the specimen are spread out toward the walls and collected within the cavity defined by the pocket. Additionally, as the vessel is spinning, a tube located within the body of the vessel to aspirate contents of the vessel that are not within the cavity (e.g., the plasma and associated proteins). The actuating device can stop the spinning of the vessel about its axis in order to add buffer into the vessel and repeat the spinning and aspiration steps described above. These steps may be repeated as many times as desired. Additional details regarding the cell washer 128 and the process of cell washing are described in PCT Application No. PCT/US2017/066312, filed on Dec. 14, 2017, entitled CELL WASHING DEVICE AND METHOD, the entirety of which is hereby incorporated by reference.

The liquid reagent housing 130 of the reagent station 108 stores a plurality of liquid labeling reagents within vials positioned in a carousel within an enclosed housing. In some examples, the enclosed housing can maintain a temperature between about 2° C. and about 8° C. to refrigerate the liquid labeling reagents. Different types of liquid labeling reagents can be stored. Additionally, different vial types containing the liquid labeling reagents can be positioned in the carousel. For example, vials having flat bottoms that need to be positioned at an angle, as well as vials having v-shaped bottoms that need to be positioned vertically.

In some examples, the vials have a piercable cap, and a lid of the liquid reagent housing 130 (e.g., a lid of the enclosed housing) comprises two openings that line up with rows on the carousel such that a probe 114 of the transfer station 112 can enter the liquid reagent housing 130 through one of the openings to pierce a vial positioned in the carousel in alignment with the opening. The probe 114 can transfer liquid labeling reagent from the vial to the well in the reaction plate comprising the sample volume of the specimen.

The dry reagent carousel 132 of the reagent station 108 stores a plurality of cartridges, each comprising a dry labeling reagent sealed within an aluminum heat seal. Different dry labeling reagents can be stored in the cartridges. As one example, the sample preparation instrument 100 can include at least two dry reagent carousels 132, each having six or more cartridges per carousel with six to twenty wells per cartridge. The probe 114 of the transfer station 112 can pierce through an impermeable, opaque seal of a cartridge and reconstitute the dry reagent contained therein with buffer. Once the dry reagent is reconstituted, the reconstituted reagent can be transferred by the probe 114 from the cartridge to the well in the reaction plate comprising the sample volume of the specimen. Alternatively, the sample volume of the specimen can be transferred directly into the cartridge containing the dry labeling reagent, and the sample can be mixed with the dry labeling reagent inside of the cartridge. The labeled sample can then be transferred to the well in the reaction plate for additional processing.

The lysing station 110 includes a carousel holding bottles comprising various types of lytic reagents. In some examples, the carousel is comprised of two half-moon shaped adaptors, where each adaptor is tailored to hold bottles of varying sizes. The tops are not pierceable, and thus the user must remove the tops of the bottles before placing the bottle on one of the adaptors in the lysing station 110. The probe 114 of the transfer station 112 can transfer a lytic reagent from a bottle to the well in the reaction plate comprising the sample volume of the specimen with added labeling reagents for incubation. In some examples, when multiple lytic reagents are required, incubation can be performed in between the addition of each lytic reagent. In further examples, the cell washer 128 can perform another wash on the sample following the addition of the lytic reagents and corresponding incubation time in order to slow down the lytic activity.

In some examples, each of the liquid reagent housing 130, the dry reagent carousel 132, and the lysing station 110 include a reader or a scanner to read machine-readable codes on the vials, cartridges, and bottles and adaptors, respectively, to maintain inventory (e.g., determine when a particular cartridge has been reconstituted and aspirated, a particular vial is low on the corresponding liquid labeling reagent, or a bottle is low on lytic reagent). If one or more of the vials, cartridges, and bottles need to be replaced, the user can access each of the liquid reagent housing 130, the dry reagent carousel 132, and the lysing station 110 by opening an entirety of a front panel of the instrument (e.g., the front panel comprising the access opening for the input station 124). For example, the front panel may slide up. In some examples, the user has to wait until operations have stopped in order to open the entirety of the front panel. For example, the user can request for the sample preparation instrument 100 to pause operation, the user can open the front panel to access and replace the vials, cartridges, and/or bottles, then the user can close the front panel and the sample preparation instrument 100 will resume operation.

In some examples, in addition to the liquid reagent housing 130, the dry reagent carousel 132, and the lysing station 110, readers or scanners can be included in the other hardware components to track the sample preparation process. Collectively, these readers or scanners can form a tracking system of the sample preparation instrument 100. For example, such tracking forms a chain of custody for the sample, whereby the user can then later determine exactly which components interacted with the sample and details about the interaction (e.g., how much and what types of reagent were added and how long were the respective incubation periods, whether the specimen and/or sample was washed, etc.).

The sample preparation instrument 100 can optionally include a bead mixer 134. The bead mixer 134 can maintain the homogeneity of a counting bead suspension contained in bottles. In some sample preparation processes, a known concentration of the counting beads can be added to a sample that is being prepared to provide a reference for determining a concentration of components in the specimen. In some examples, the counting bead bottle includes an evaporation cap to minimize evaporation of the counting bead suspensions. The counting bead suspension bottles can include a machine-readable code that is scanned when utilized during a sample preparation process to facilitate tracking of the sample preparation process.

In some examples, the reaction station 109, where the labeling reagents and lytic reagents come into contact with the sample volume of the specimen (e.g., within the wells of the reaction plate), can include the plate mixer 136. The plate mixer 136 is an orbital shaker, for example, that can hold one or more plates. For example, the plate mixer 136 can hold the reaction plate comprising the wells into which the sample volume of the specimen, labeling reagents, and lytic reagents are dispensed. In some examples, the plate mixer 136 moves in a circular or elliptical motion to mix the sample volume of the specimen with the labeling reagents, and mix the lytic reagents with the sample volume of the specimen/labeling reagents during the respective incubation periods.

The probe wash station 138 washes the probe 114 of the transfer station 112 any time the probe 114 touches the specimen, a labeling reagent, a lytic reagent, or any other type of liquid to prevent any contamination. To wash the probe 114, the probe 114 can be inserted into a well, and buffer can be added to surround the probe 114 within the well.

After the labeling reagents and lytic reagents are added to the sample volume of the specimen in the well of the reaction plate and incubated, the cell washer 128 can optionally perform another wash. Following the incubation or the optional wash, the output station 140 can receive the prepared sample to provide as output 104. In some examples, the output station 140 includes an output carousel comprising a plurality of clean tubes, and the probe 114 of the transfer station 112 transfers the prepared sample from one of the well in the reaction plate or the cell washer 128 to a clean tube within the output carousel. A user can choose to remove the output carousel from the sample preparation instrument 100 when the output carousel is full or when the output carousel is partially full. For example, a slide-out drawer on a left hand side panel of the sample preparation instrument 100 can be utilized by the user to remove one or more tubes comprising the prepared sample at any time, even when the sample preparation instrument 100 is operating. For example, the user can request access, and the sample preparation instrument 100 will then enable the slide-out drawer to be accessed. In some instances, there can be a delay between the request and the time when access is granted dependent on operations currently ongoing within the sample preparation instrument 100. In other examples, the output station 140 includes a clean reaction plate and/or clean well in the reaction plate into which the prepared sample is transferred by the probe 114.

In addition to the hardware components described in FIG. 4, FIG. 5 further depicts a waste container 142, a diluent reagent container 144, and a condensation collector 146. Waste associated with the sample preparation process, including the specimen waste from the cell concentration estimator 106 is dispensed to the waste container 142. The diluent reagent can be used in several steps through the preparation process, including the cell concentration estimation and to reconstitute dry reagent, among other examples. The condensation collector 146 can collect any condensation resulting from a cooling of the labeling reagents (e.g., generated by the liquid reagent housing 130).

FIG. 6 is a block diagram of basic hardware components of an example sample preparation and analysis instrument 150. The sample preparation and analysis instrument 150 includes similar components as the sample preparation instrument 100, such as the cell concentration estimator 106, the reagent station 108, the reaction station 109, and the lysing station 110, described above in detail with respect to FIGS. 3 through 5. Additionally, the sample preparation and analysis instrument 150 includes a sample analyzer 152 that receives the prepared sample as input and performs an analysis on the prepared sample to provide sample analysis results as output 154. In some examples, the sample analyzer 152 is a flow cytometer.

FIG. 7 is an example computing device 116 that can be used to implement aspects of the present disclosure. The computing device 116 can be used to execute the operating system, application programs, and software modules (including the software engines) described herein.

The computing device 116 includes, in some embodiments, at least one processing device 120, such as a central processing unit (CPU). A variety of processing devices are available from a variety of manufacturers, for example, Intel or Advanced Micro Devices. In this example, the computing device 116 also includes a system memory 118, and a system bus 160 that couples various system components including the system memory 118 to the processing device 120. The system bus 160 is one of any number of types of bus structures including a memory bus, or memory controller; a peripheral bus; and a local bus using any of a variety of bus architectures.

The system memory 118 includes read only memory 162 and random access memory 164. A basic input/output system 166 containing the basic routines that act to transfer information within computing device 116, such as during start up, is typically stored in the read only memory 162.

The computing device 116 also includes a secondary storage device 168 in some embodiments, such as a hard disk drive, for storing digital data. The secondary storage device 168 is connected to the system bus 160 by a secondary storage interface 170. The secondary storage device 168 and their associated computer readable media provide non-volatile storage of computer readable instructions (including application programs and program modules), data structures, and other data for the computing device 116.

Although the exemplary environment described herein employs a hard disk drive as a secondary storage device, other types of computer readable storage media are used in other embodiments. Examples of these other types of computer readable storage media include flash memory cards, digital video disks, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 168 or system memory 118, including an operating system 172, one or more application programs 174, other program modules 176 (such as the software engines described herein), and program data 178. One example application program includes a panel authoring and management application. The computing device 116 can utilize any suitable operating system, such as Microsoft Windows™, Google Chrome™ OS, Apple OS, Unix, or Linux and variants and any other operating system suitable for a computing device. Other examples can include Microsoft, Google, or Apple operating systems, or any other suitable operating system.

In some embodiments, a user provides inputs to the computing device 116 through one or more input devices 180. Examples of input devices 180 include a keyboard 182, mouse 184, microphone 186, and touch sensor 188 (such as a touchpad or touch sensitive display). Other embodiments include other input devices 180. The input devices are often connected to the processing device 120 through an input/output interface 190 that is coupled to the system bus 160. These input devices 180 can be connected by any number of input/output interfaces, such as a parallel port, serial port, game port, or a universal serial bus. Wireless communication between input devices and the input/output interface 190 is possible as well, and includes infrared, BLUETOOTH® wireless technology, IEEE 802.11a/b/g/n, cellular, ultra-wideband (UWB), ZigBee, LoRa, or other radio frequency communication systems in some possible embodiments.

In this example embodiment, a display device 192, such as a monitor, liquid crystal display device, projector, or touch sensitive display device, is also connected to the system bus 160 via an interface, such as a video adapter 194. In addition to the display device 192, the computing device 116 can include various other peripheral devices (not shown), such as speakers or a printer.

When used in a local area networking environment or a wide area networking environment (such as the Internet), the computing device 116 is typically connected to the network through a network interface 196, such as an Ethernet interface. Other possible embodiments use other communication devices. For example, some embodiments of the computing device 116 include a modem for communicating across the network.

The computing device 116 typically includes at least some form of computer readable media. Computer readable media includes any available media that can be accessed by the computing device 116. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 116.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device 116 illustrated in FIG. 7 is also an example of programmable electronics, which may include one or more such computing devices, and when multiple computing devices are included, such computing devices can be coupled together with a suitable data communication network so as to collectively perform the various functions, methods, or operations disclosed herein.

Figure 8:
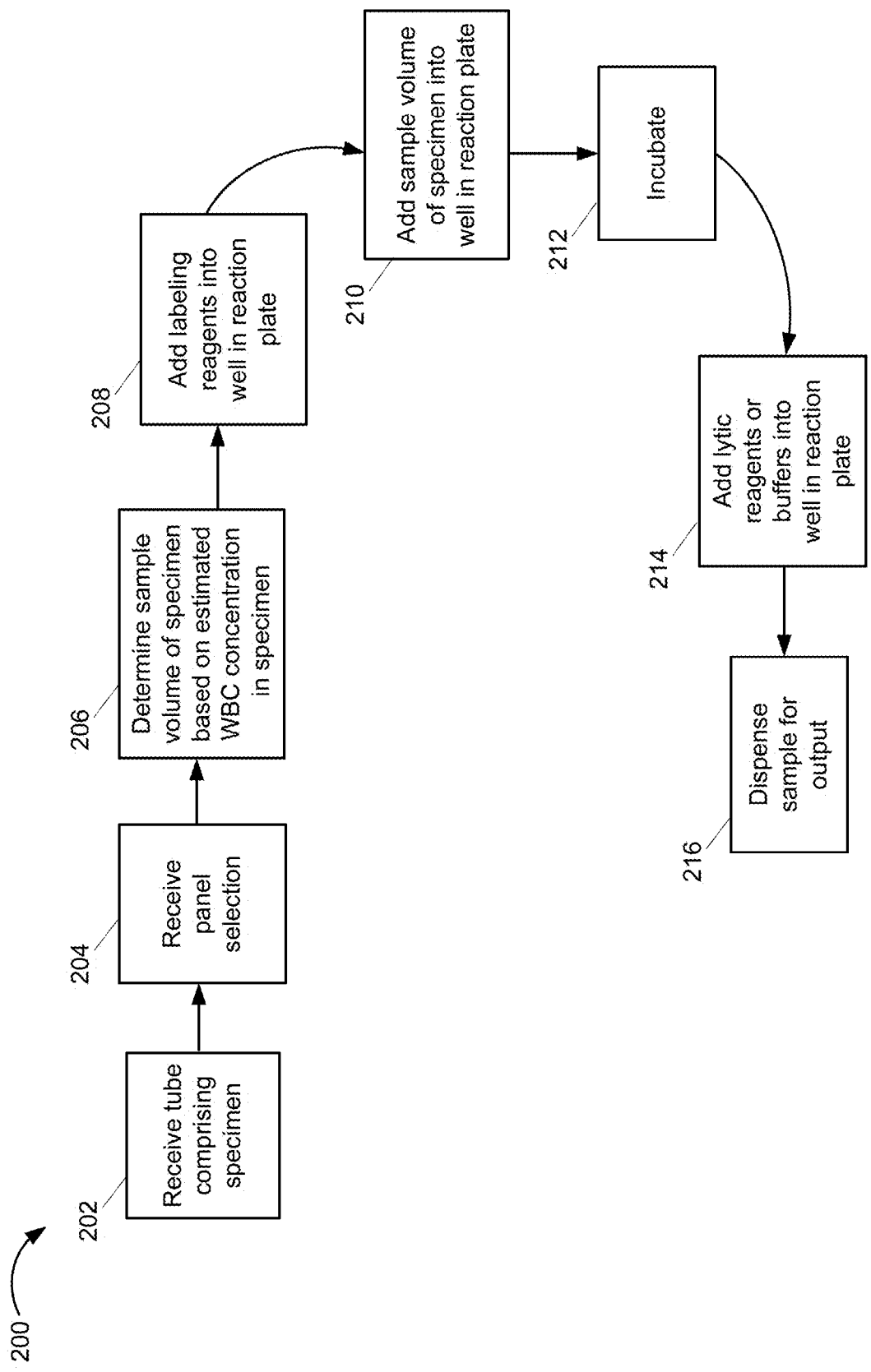
FIG. 8 schematically illustrates an example sample preparation process for a specimen.

FIG. 8 schematically illustrates an example sample preparation process 200 for the specimen. The sample preparation process 200 can be performed by the sample preparation instrument 100. Prior to the sample preparation instrument 100 performing the sample preparation process 200, panels (e.g., defined workflows for preparing samples of different types of specimen for different types of analysis) are created by the user through the panel authoring and management application, for example, that is executed on a remote computing device, such as a laptop, tablet, or desktop, among other similar devices. The panels can then be transmitted to the sample preparation instrument 100 via a wired or wireless connection, such as via a USB connector, a Local Area Network (LAN), or over the Internet. In some examples, the defined workflows of the panels each include a set of predefined rules associated with the preparation of the specimen, including processing requirements such as sample volumes of the specimen based on white blood cell concentrations, dilution requirements, labeling reagent volumes, lytic reagent volumes, incubation time periods, and other similar rules. The panels can be stored in the memory 118 of the computing device 116 of the sample preparation instrument 100.

The sample preparation process 200 can begin at operation 202, where at least one tube comprising the specimen is received. In some examples, the tube is a capped tube received in an input cassette at the input station 124 that is then rocked via a rocking mechanism of the input station 124 to maintain suspension of the specimen within the tube. The input cassette can hold multiple capped tubes, where one or more of the capped tubes comprise different specimens (e.g., each capped tube can include a specimen associated with a different person or patient). In other examples, the tube is an open-top tube comprising the specimen that is either received in an input cassette at the input station 124 that is not rocked or is received at the single tube loader 126. In some examples, the open-top tube is received when the user manually pre-processes the specimen. In either of the above examples, the tube comprising the specimen can include a machine-readable code that can be read by a scanner or reader of the input station 124 or the single tube loader 126. The machine-readable code can identify the specimen. Alternatively, the specimen identifier can be manually entered via the user interface of the touch display 122, for example.

At operation 204, a panel selection can be received through the user interface of the touch display 122. For example, the user interface can display the identity of the specimen within the tube (e.g., the specimen identifier) and one or more of the panels that can be selected for pairing with the specimen. Once one or more of the displayed panels are selected for the specimen within the tube, the sample preparation instrument 100 can process a sample of the specimen according to a workflow defined for the panel as described in operations 206 to 216. In some examples, the workflow for the panel, including the set of predefined rules, are retrieved from the memory 118 in response to the receipt of the panel selection at operation 204.

At operation 206, a sample volume of the specimen is determined based on a white blood cell concentration in the specimen and the set of predefined rules. For example, the set of predefined rules can include one or more ranges of white blood cell concentration values and corresponding sample volumes of the specimen for each range. The sample volume that corresponds to the range into which the white blood cell concentration in the specimen falls is the determined sample volume of the specimen.

In some examples, the cell concentration estimator 106 estimates the white blood cell concentration in the specimen based on an estimated white blood cell concentration in an aliquot of the specimen. For example, the probe 114 of the transfer station 112 pierces the capped tube comprising the specimen at the input station 124 or inserts into the open-top tube comprising the specimen at the input station 124 or the single tube loader 126. The aliquot of the specimen is aspirated by the probe 114 and transferred to the cell concentration estimator 106. The cell concentration estimator 106 can employ an optical method, an electrical resistance method, a flow cytometry method, or other similar method known to one of ordinary skill in the art to estimate the white blood cell concentration in the aliquot, which is representative of the estimated white blood cell concentration in the specimen as a whole. The aliquot of the specimen is then released as waste from the cell concentration estimator 106. The processing device 120 can automatically determine the sample volume of the specimen based on the estimated white blood cell concentration and the set of predefined rules.

In other examples, the white blood cell concentration in the specimen used for the sample volume determination is received from a source external to the sample preparation instrument 100 and is manually entered via the user interface of the touch display 122 or is received via a lab information system (LIS) accessible by the sample preparation instrument 100. Alternatively, the sample volume determination can be made by the user based on the received white blood cell concentration and knowledge of the set of predefined rules, and the sample volume manually entered via the user interface of the touch display 122.

At operation 208, one or more labeling reagents are added into a well of a reaction plate, or other similar container. A volume and a type of the labeling reagent to be added can be specified by the selected panel (e.g., within the set of predefined rules). The labeling reagents can target a particular constituent of the specimen to facilitate analysis of that constituent. In some examples, the reaction plate is a component of the reagent station 108, where the labeling reagents are stored. In other examples, the reaction plate is a component of the reaction station 109, separate from the reagent station 108.

In some examples, the labeling reagents are liquid labeling reagents stored within vials positioned in rows of a carousel. The carousel can be enclosed in the liquid reagent housing 130 that is maintained at a controlled temperature. To add the liquid labeling reagents to the well in the reaction plate, the carousel can be positioned such that the vial comprising the appropriate liquid labeling reagent is underneath an opening within a lid of the liquid reagent housing 130. The probe 114 of the transfer station 112 can enter the liquid reagent housing 130 through the opening, pierce the vial, aspirate the liquid labeling reagent from the vial, and dispense the liquid labeling reagent into the well in the reaction plate.

Additionally and/or alternatively, the labeling reagents can be dry labeling reagents stored within cartridges of the dry reagent carousel 132 that are reconstituted into a liquid prior to adding to the well in the reaction plate. For example, to add the liquid labeling reagents to the well, the probe 114 of the transfer station 112 can pierce through an impermeable, opaque seal of a cartridge and reconstitute the dry reagent contained therein with buffer. Once the dry reagent is reconstituted, the reconstituted reagent can be aspirated from the cartridge by the probe 114 of the transfer station 112 and dispensed into the well in the reaction plate.

In some examples, a machine-readable code on the vial or cartridge from which the liquid or reconstituted dry labeling reagent was aspirated can be scanned to facilitate tracking of the current sample preparation process and provide inventory-related information (e.g., how much volume of labeling reagent remains following the aspiration).

Once the labeling reagents have been added to the well in the reaction plate at operation 208, the sample volume of the specimen determined at operation 206 is added to the well in the reaction plate at operation 210. For example, the probe 114 of the transfer station 112 can aspirate the sample volume of the specimen from the tube at the input station 124 or the single tube loader 126. As one example, a sample volume of 400 µL of the specimen can be dispensed equally into four wells that already have a labeling agent dispensed within the wells.

At operation 212, the sample volume of the specimen and the labeling reagents can be incubated within the well of the reaction plate. The incubation can be for a predetermined time period specified by the panel, for example. The time period can be based on the type of the labeling reagents. In some examples, the reaction plate is positioned on the plate mixer 136, which can move in a circular or elliptical motion to mix the sample volume of the specimen with the labeling reagents for a portion of the incubation time period.

At operation 214, one or more lytic reagents or buffers stored within the lysing station 110 are added into the well of the reaction plate (e.g., within the wells comprising the sample volume of the specimen and labeling reagents). A volume and a type of the lytic reagents or buffers to be added can be specified by the panel (e.g., within the set of predefined rules). Lytic reagents can destroy particular constituents of the specimen that can interfere with the analysis. For example, when the specimen is whole blood, and the analysis is a leukemia or lymphoma panel focusing on subsets of white blood cells, lytic reagents are added to destroy red blood cells that can interfere with the analysis of the subsets of white blood cells during the panel.

To add the lytic reagents into the well of the reaction plate, the probe 114 of the transfer station 112 can enter into a topless bottle comprising an appropriate lytic reagent that is held by an adaptor of the lysing station 110 to aspirate the lytic reagent. The lytic reagent is then dispensed into wells of the reaction plate comprising the sample volume of the specimen and the labeling reagents. In some examples, a machine-readable code on the bottle from which the lytic agent is aspirated and/or the adaptor holding the bottle can be scanned to facilitate tracking of the current sample preparation process and provide inventory-related information (e.g., how much volume of lytic reagent remains in the bottle following the aspiration). In other examples, buffers rather than lytic reagents are added based on the specimen type and the panel selected.

At operation 216, a sample from each well of the reaction plate comprising the sample volume of the specimen, labeling reagents, and lytic reagents or buffers can be dispensed for output. In some examples, the sample from each well is aspirated by the probe 114 of the transfer station 112 and dispensed into a clean tube arranged in an output carousel of the output station 140. In other examples, the sample from each well is aspirated by the probe 114 of the transfer station 112 and dispensed into a clean well of a multi-well plate at the output station 140. The user of the sample preparation instrument can then remove individual tubes, the output carousel, or the multi-well plate from the output station 140.

Figure 9:
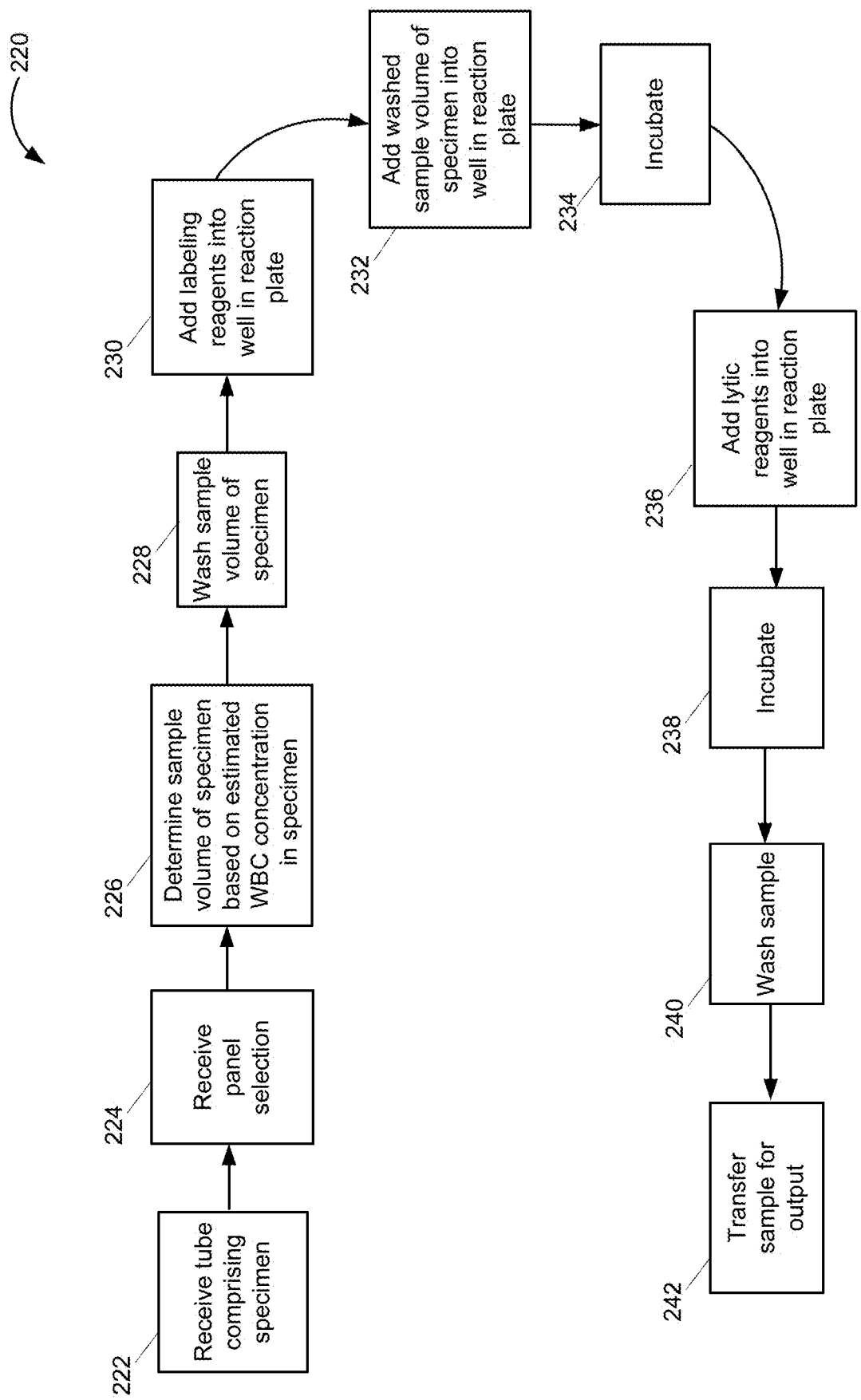
FIG. 9 schematically illustrates another example sample preparation process for a specimen.

FIG. 9 schematically illustrates another example sample preparation process 220 for the specimen. The sample preparation process 220 can be performed by the sample preparation instrument 100. Similar to operations 202, 204, and 206 of the sample preparation process 200 described in detail above in conjunction with FIG. 8, the sample preparation process 220 begins with receiving a tube comprising the specimen at operation 224, receiving a panel selection at operation 224, and determining a sample volume of the specimen based on an estimated white blood cell concentration in the specimen at operation 226.

Once the appropriate sample volume of the specimen has been determined at operation 226, the probe 114 of the transfer station 112 can either pierce the capped tube comprising the specimen at the input station 124 or insert into the open-top tube comprising the specimen at the single tube loader 126 to aspirate the sample volume of the specimen. The sample volume of the specimen can be dispensed by the probe 114 into a vessel of the cell washer 128, and the sample volume of the specimen is washed at operation 228. Washing the sample volume of the specimen can help remove constituents of the sample that are not necessary for, or must be removed prior to analysis. For example, if the specimen is whole blood comprising red blood cells, white blood cells, platelets, plasma and associated proteins, washing the sample volume of the specimen can remove the plasma and associated proteins.

To wash the sample volume of the specimen, a washing liquid, such as a buffer solution can be dispensed into a body of the vessel via a conduit extending into the vessel. In some examples, the vessel is spun about the axis upon activation of an actuating device of the cell washer 128. As the vessel is being spun about its axis, the heavier blood cells in the sample volume of the specimen are spread out toward the walls of the vessel and collected within a cavity defined by a pocket of the vessel, and the contents of the vessel that are not within the cavity can be aspirated through the conduit. The actuating device can stop the spinning of the vessel about its axis in order to add more wash liquid into the vessel and suspend the cells collected within the pocket. These steps can then be repeated as many times as desired.

Similar to operations 208, 210, 212, and 214 of the sample preparation process 200 described in detail above in conjunction with FIG. 8, the sample preparation process 220 continues with: the addition of one or more labeling reagents to a well of the reaction plate at operation 230; the addition of the washed sample volume of the specimen into the well of the reaction plate containing the labeling reagents at operation 232; incubation of the washed sample volume of the specimen with the labeling reagents at operation 234; and the addition of lytic reagents into the well of the reaction plate containing the washed sample volume of the specimen and the labeling reagents at operation 236. At operation 238, the washed sample volume of the specimen, the labeling reagents, and the lytic reagents can be incubated within the well of the reaction plate. The incubation can be for a predetermined time period specified by the panel, for example. The time period can be based on the type of the lytic reagents. In some examples, the reaction plate is positioned on the plate mixer 136, which can move in circular or elliptical motion to mix the washed sample volume of the specimen, the labeling reagents, and the lytic reagents and hold this mixture during the incubation time period. In some examples, when multiple lytic reagents are required, the lytic reagents are added and incubated one at a time.

At operation 240, a sample comprising the washed sample volume of the specimen, the labeling reagents, and the lytic reagents within each well can be washed. For example, the probe 114 of the transfer station 112 can aspirate the sample from a well and transfer to the cell washer 128 for washing. This operation 240 can be repeated for each sample containing well, and the washing can be performed by the cell washer 128 in a similar manner to the washing performed at operation 228. The washing can help slow down the lytic activity caused by the addition of the lytic agents and incubation thereof at operation 236 and 238, respectively, to avoid destruction of constituents targeted for analysis (e.g., to avoid destruction of the white blood cells). Additionally, the washing can remove red blood cell debris. In other example sample preparation workflows, a no lyse-wash protocol can be followed.

Similar to operation 216 of the sample preparation process 200 described in detail above in conjunction with FIG. 8, the sample preparation process 220 ends with the sample from each well being dispensed for output at operation 242.

Figure 10:
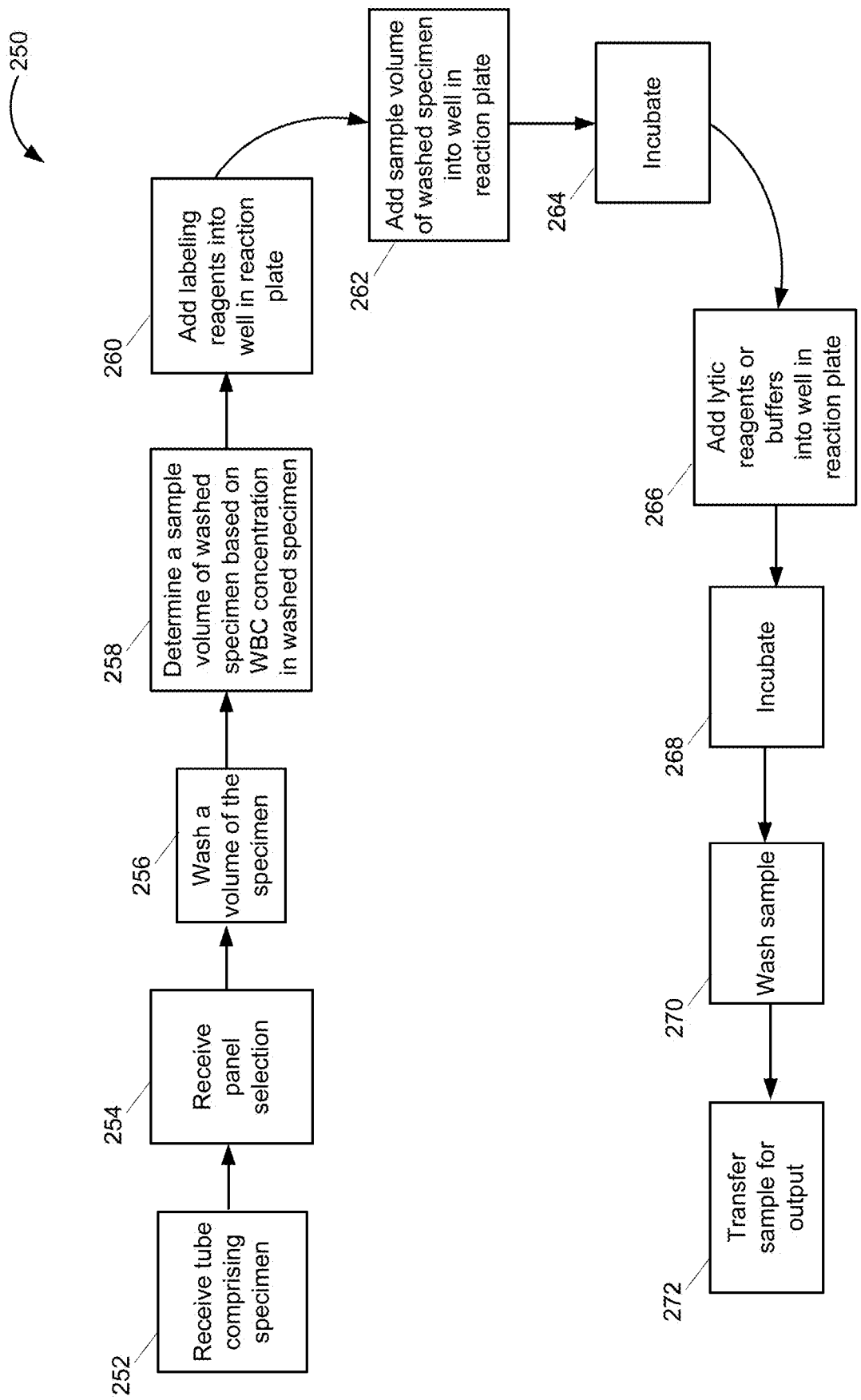
FIG. 10 schematically illustrates a further example sample preparation process for a specimen.

FIG. 10 schematically illustrates a further example sample preparation process 250 for the specimen. The sample preparation process 250 can be performed by the sample preparation instrument 100. Similar to operations 202 and 204 of the sample preparation process 200 described in detail above in conjunction with FIG. 8, the sample preparation process 250 begins with receiving a tube comprising the specimen at operation 252 and receiving a panel selection at operation 254. At operation 256, a volume of the specimen can be washed by the cell washer 128 similar to the washing performed at operation 228 of the sample preparation process 220 described in detail with reference to FIG. 9. At operation 258, a sample volume of the washed specimen is determined based on an estimated white blood cell concentration in the specimen, similar to the determination performed at operation 206 described in detail above in conjunction with FIG. 8. The volume of the specimen washed at operation 256 is a larger volume than the potential sample volumes that could be determined at operation 258 to ensure that the volume of the washed specimen is greater than the determined sample volume of the washed specimen.

Similar to operations 208, 210, 212, and 214 of the sample preparation process 200 described in detail above in conjunction with FIG. 8, the sample preparation process 250 continues with: the addition of one or more labeling reagents to a well of the reaction plate at operation 260; the addition of the sample volume of the washed specimen to the well of the reaction plate containing the labeling reagents at operation 262; incubation of the sample volume of the washed specimen with the labeling reagents at operation 264; and the addition of lytic reagents or buffers into the well of the reaction plate containing the sample volume of the washed specimen and the labeling agents at operation 266.

Similar to operations 238 and 240 described in detail above in conjunction with FIG. 9, the sample preparation process 250 continues with incubation of the sample volume of the washed specimen, the labeling reagents, and the lytic reagents or buffers within the well of the reaction plate at operation 268, and washing of a sample comprising the sample volume of the washed specimen, the labeling reagents, and the lytic reagents or buffer agents within each well at operation 270. The sample preparation process 250 then ends with the sample from each well being dispensed for output at operation 272, similar to operation 216 of the sample preparation process 200 described in detail above in conjunction with FIG. 8.

Figure 11:
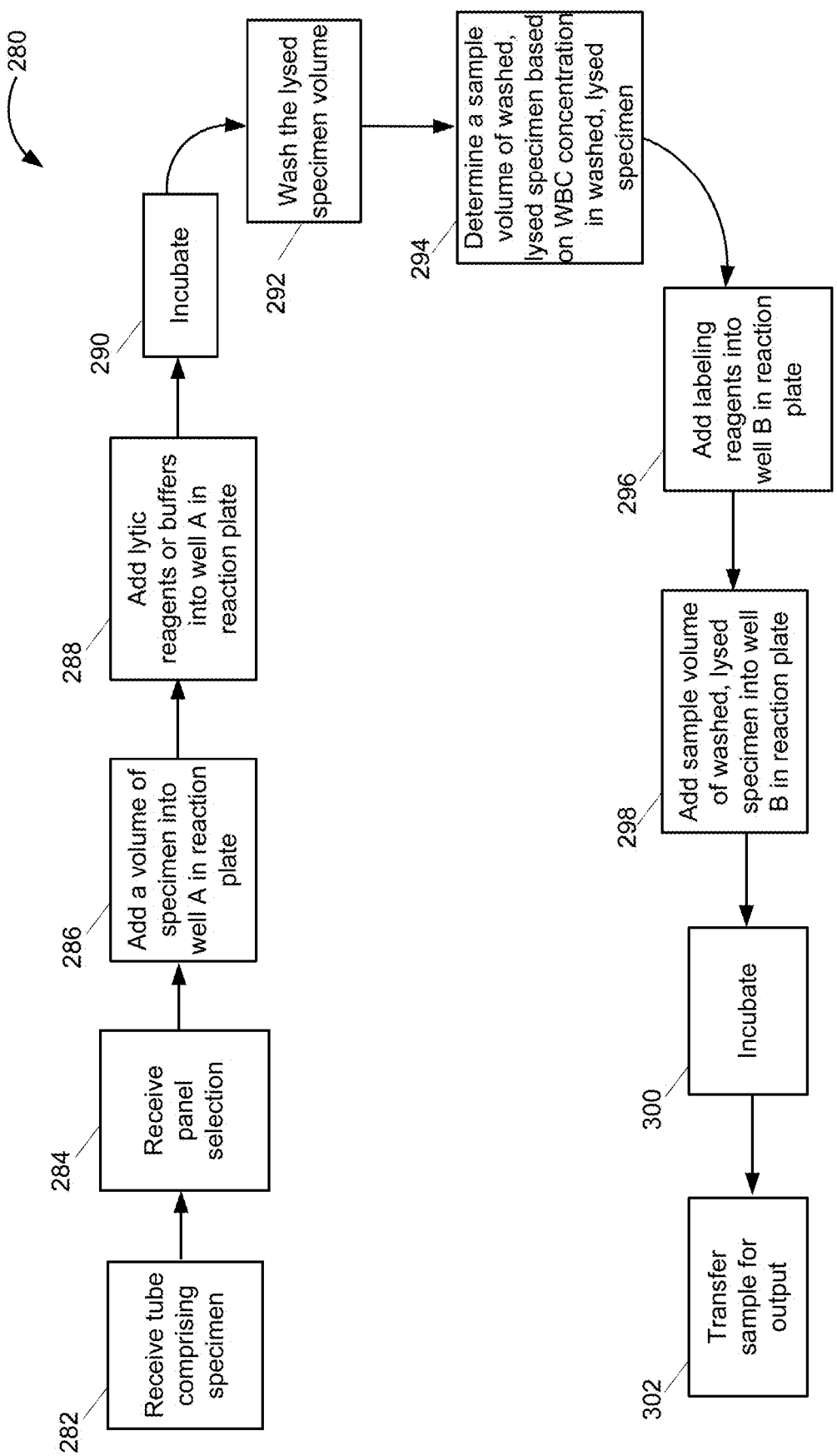
FIG. 11 schematically illustrates a yet further example sample preparation process for a specimen.

FIG. 11 schematically illustrates a further example sample preparation process 280 for the specimen. The sample preparation process 280 can be performed by the sample preparation instrument 100. Similar to operations 202 and 204 of the sample preparation process 200 described in detail above in conjunction with FIG. 8, the sample preparation process 280 begins with receiving a tube comprising the specimen at operation 282 and receiving a panel selection at operation 284. At operation 286, a volume of the specimen is added into a first well (e.g., well A) in the reaction plate. At operation 288, one or more lytic reagents are added into the first well (e.g., the well including the volume of the specimen). At operation 290, the volume of the specimen and the lytic reagents can be incubated. In other examples, buffers rather than lytic agents can be added at operation 288 and incubated with the volume of the specimen at operation 290.

At operation 292, the lysed volume of the specimen can be washed by the cell washer 128 similar to the washing performed at operation 228 of the sample preparation process 220 described in detail with reference to FIG. 9. At operation 294, a sample volume of the washed, lysed specimen is determined, similar to the determination performed at operation 206 described in detail above in conjunction with FIG. 8.

At operation 296, one or more labeling reagents are added to a second well (e.g., well B) of the reaction plate. At operation 298, the sample volume of the washed, lysed specimen is added to the second well in the reaction plate (e.g., the second well containing the labeling reagents). The sample volume of lysed specimen and the labeling reagents added to the second well are then incubated at operation 300. The sample preparation process 280 then ends with the sample from each well being dispensed for output at operation 302, similar to operation 216 of the sample preparation process 200 described in detail above in conjunction with FIG. 8.

FIGS. 8, 9, 10, and 11 provide non-limiting examples of different sample preparation processes having various steps and an order thereof. Other sample preparation processes are possible comprising additional combinations of the steps or operations discussed herein.

Figure 12:
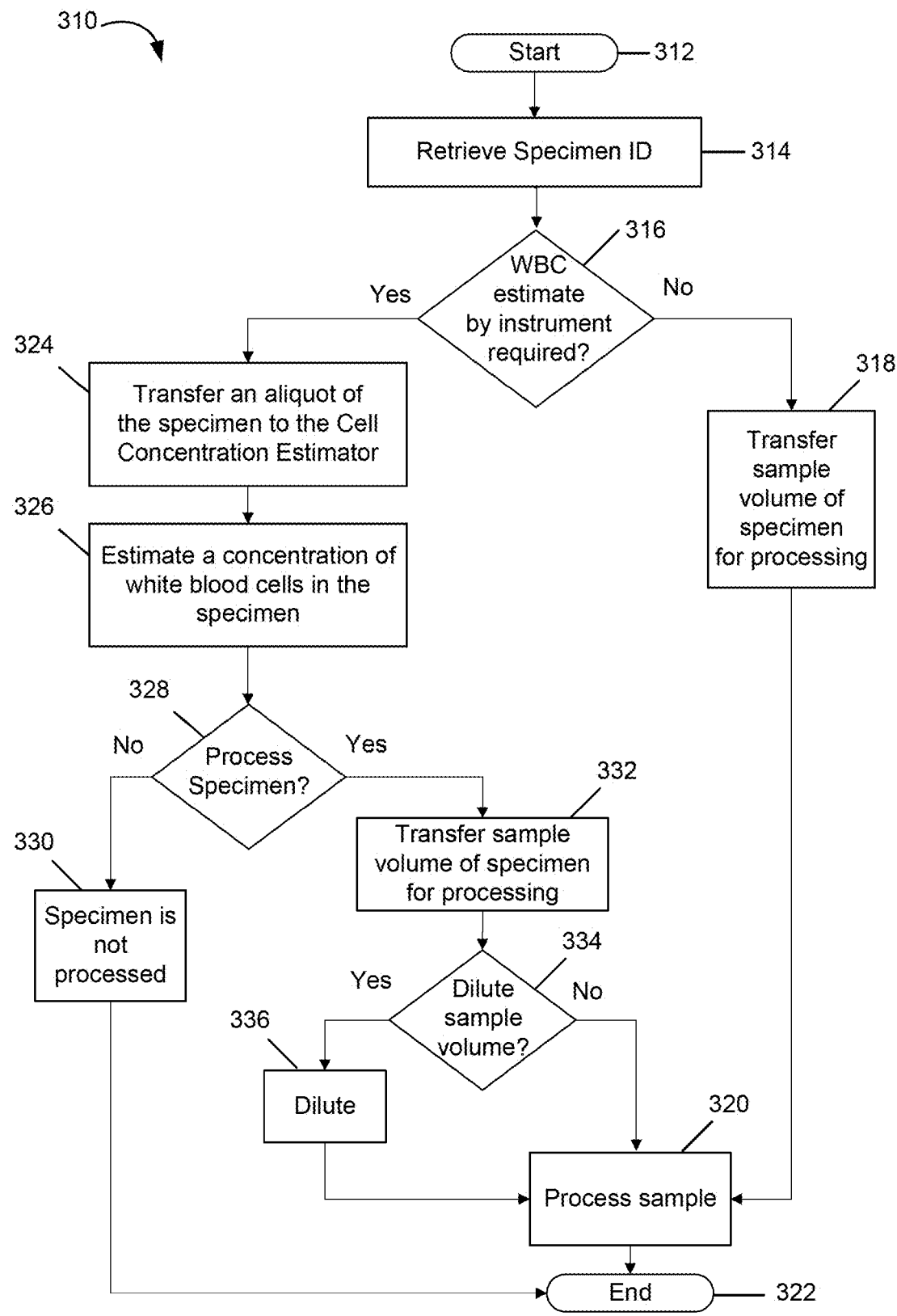
FIG. 12 is a process flow diagram illustrating a method for preparing a sample of a specimen for analysis.

FIG. 12 is a process flow diagram illustrating a method 310 for preparing a sample of a specimen for analysis. The method 310 can be performed by the sample preparation instrument 100. In some examples, the sample preparation instrument 100 is housed in a laboratory providing sample analysis services, such as flow cytometry services. The method 310 starts at operation 312 after the specimen is received at the input station 124 or the single tube loader 126 of the sample preparation instrument 100. In some examples, the specimen can be received within a tube that is labeled with a machine-readable code.

At operation 314, a specimen identifier (ID) of the specimen is retrieved. For example, a scanner or reader at the input station 124 or the single tube loader 126 can scan or read the machine-readable code on the tube to retrieve the specimen ID. The machine-readable code can be a barcode, a QR code, or a Radio Frequency Identification (RFID) tag, among other similar examples. In other examples, the specimen ID can be manually entered by a user through a user interface of the touch display 122. The user can select a panel to match or pair with the specimen ID, where the panel defines a workflow or operations to prepare a sample for a particular type of specimen and analysis to be performed on the specimen, including a set of predefined rules. The set of predefined rules for the selected panel can be retrieved from the memory 118 of the computing device 116. Example predefined rules can include one or more of whether the concentration of white blood cells for the specimen is to be estimated by the sample preparation instrument 100, a minimum concentration of white blood cells, a maximum concentration of white blood cells, a sample volume of the specimen for one or more ranges of concentrations of white blood cells between the minimum concentration and maximum concentration, and whether to dilute the sample volume of the specimen, among other examples.

Based on the set of predefined rules, a determination is made at decision 316 as to whether the concentration of white blood cells in the specimen is to be estimated by the sample preparation instrument 100. If the sample preparation instrument 100 does not need to estimate the white blood cell concentration, a sample volume of the specimen is transferred by the probe 114 of the transfer station 112 from the input station 124 or the single tube loader 126 at operation 318 for processing.

In some examples, the sample preparation instrument 100 does not need to perform the white blood cell concentration estimate because a white blood cell concentration for the specimen has already been obtained from which the sample volume of the specimen can be determined. As one example, the laboratory may also house a hematology instrument that is separate from the sample preparation instrument 100, where the hematology instrument analyzes the specimen to determine the white blood cell concentration. As another example, a laboratory technician can prepare a smear and employ microscopy methods for counting a number of white blood cells and estimating a concentration based thereon. As a further example, another laboratory, such as a hematology laboratory, can analyze the specimen and provide the white blood cell concentration to the current laboratory housing the sample preparation instrument 100.

In the above examples, the obtained white blood cell concentration can then be manually input to the sample preparation instrument 100 or can be accessed by the sample preparation instrument 100 through a lab information system (LIS). When the white blood cell concentration is received by the sample preparation instrument 100, the sample volume of the specimen to be prepared for analysis can be determined. In some examples, the determination is made based on the set of predefined rules. For example, the sample volume corresponding to a range of white blood cell concentration values into which the white blood cell concentration for the specimen falls is determined to be the sample volume of the specimen. In alternative examples, the sample volume of the specimen rather than the obtained white blood cell concentration can be manually input into the sample preparation instrument 100 by a laboratory technician (e.g., after the laboratory technician references the set of predefined rules and compares to the obtained white blood cell concentration).

Once the sample is processed at operation 320, the method ends at operation 322. Processing the sample at operation 320 includes at least adding one or more labeling agents and one or more lytic agents (or buffers) to the sample volume of the specimen. Processing can also involve one or more cell washes and incubation periods. Example processing steps are described in detail above in conjunction with FIGS. 8, 9, 10, and 11.

If at decision 316 a determination is made that the instrument does need to estimate the white blood cell concentration for the specimen, an aliquot of the specimen is transferred by the probe 114 of the transfer station 112 from the input station 124 or the single tube loader 126 to the cell concentration estimator 106 at operation 324. The aliquot transferred is about 10 microliters (μL) to about 50 μL of the specimen. The cell concentration estimator 106 can implement one or more of an optical method, an electrical resistance method, or a flow cytometry method, among other methods, to estimate the concentration of white blood cells in the aliquot, which is representative of the concentration of the white blood cells in the specimen, at operation 326. The sample is released from the cell concentration estimator 106 to a waste container, such as the waste container 142.

The cell concentration estimator 106 provides the white blood cell concentration estimate to the computing device 116 of the sample preparation instrument 100, where the processing device 120 determines whether to process the specimen at decision 328 based on the white blood cell concentration estimate and the set of predefined rules. If a determination is made not to process the specimen at decision 328, the specimen is not processed at operation 330 and the method ends at operation 322. In some examples, a determination is made not to process the specimen if the white blood cell concentration estimate is at or below the minimum concentration set by the predefined rules or the white blood cell concentration estimate is at or above the maximum concentration set by the predefined rules.

If a determination at decision 328 is made to process the specimen, a sample volume of the specimen is aspirated, transferred, and dispensed by the probe 114 of the transfer station 112 from the tube in the input station 124 or the single tube loader 126 for processing at operation 332. The sample volume of the specimen is determined based on the white blood cell concentration estimate and the set of predefined rules. For example, the sample volume corresponding to the range of white blood cell concentration values into which the estimate falls is determined to be the sample volume of the specimen.

At decision 334, a determination whether to dilute the sample volume of the specimen is made based on the set of predefined rules. If the sample volume of the specimen is not to be diluted, a sample is processed at operation 320 by at least adding one or more labeling agents and one or more lytic agents (or buffers), for example, to the sample volume of the specimen, and the method ends at operation 322. If the sample volume of the specimen is to be diluted, the sample volume of the specimen is diluted at operation 336. In some examples, the sample volume of the specimen is diluted in order to achieve a specified volume for labeling. To provide an example, based on the type of analysis, the specified volume of the specimen for labeling is 200 μL. However, in a scenario where the white blood cell concentration estimate is high, the determined sample volume of the specimen may be only 50 μL. Therefore, in order to maintain the specified volume of the specimen at 200 μL, the sample volume of specimen is diluted with an additional 150 μL of buffer, for example. Once the sample volume of the specimen is diluted at operation 336, the sample is processed at operation 320 by at least adding one or more labeling agents and one or more lytic agents (or buffers), for example, to the sample volume of the specimen, and the method ends at operation 322.

Figure 13:
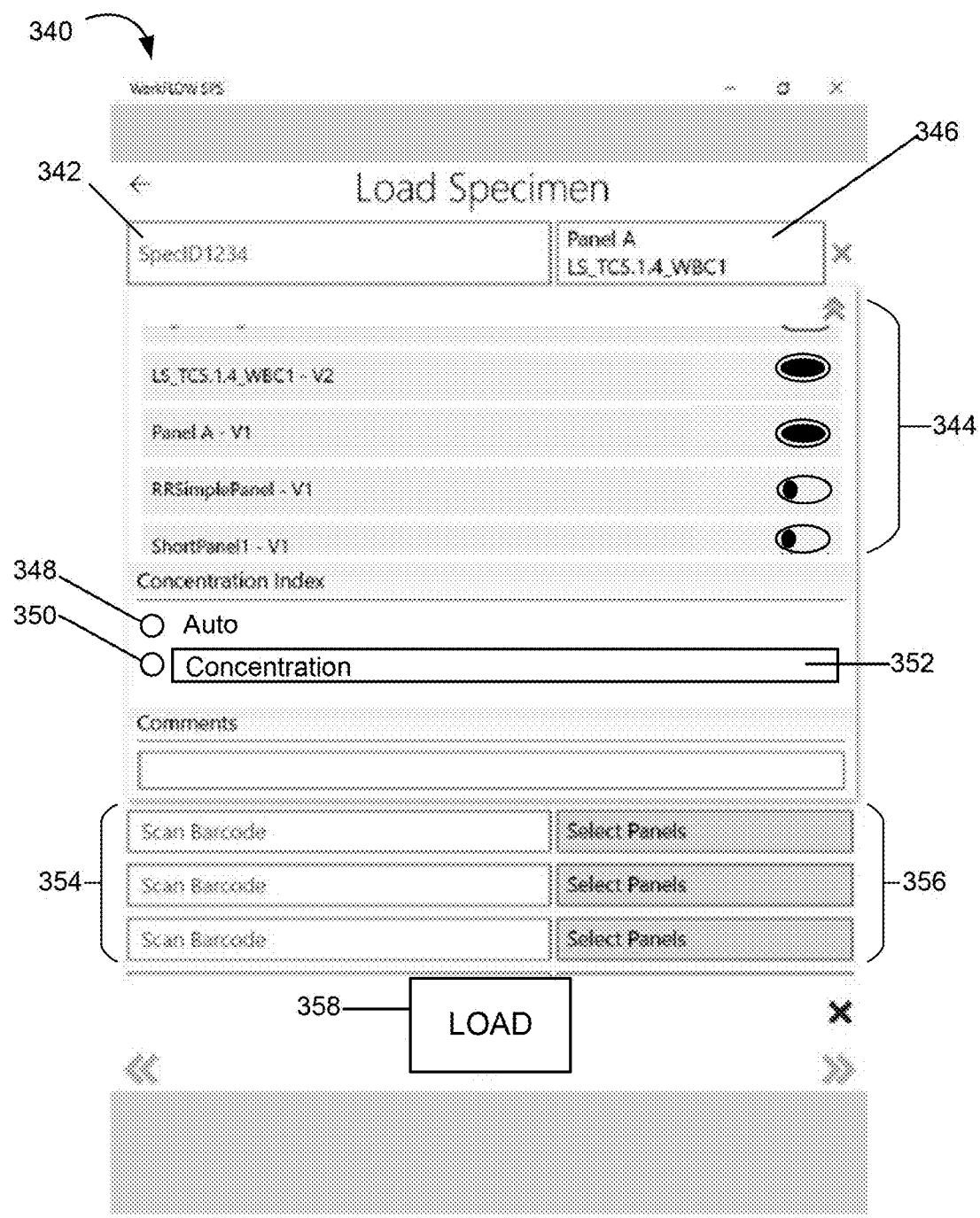
FIG. 13 is an example specimen loading user interface.

FIG. 13 is an example specimen loading user interface 340. The user interface 340 can be displayed on the touch display 122 of the sample preparation instrument 100. In some examples, a user can add one or more specimen tubes, each comprising machine-readable codes, to an input cassette. The user can then load the input cassette in the input station 124 of the sample preparation instrument 100 or hold the input cassette in his or her hand. The machine-readable codes on the tubes are scanned within the input station 124 or manually by the user to retrieve specimen identifiers from the machine-readable codes as described in operation 314 of the method 310. The retrieved specimen IDs are provided to the computing device 116 of the sample preparation instrument 100. The user can then load the input cassette into the input station 124 of the sample preparation instrument 100 if it was not loaded already.

The user interface 340 will display a specimen identifier 342 for a tube that was scanned. In some examples, the user can use a menu 344 to assign one or more panels to the specimen within the tube associated with the specimen identifier 342. As illustrated, the menu 344 is a drop down menu that includes toggles that slide from one side to the other to assign the panel to the specimen. Other types of menus and/or similar buttons or selection options can be provided within the menu 344. The panels displayed within the menu 344 can include panels previously created using a panel authoring and management application. For example, the panel authoring and management application can execute on a remote computing device separate from the sample preparation instrument 100, and any panels created are transmitted to the sample preparation instrument over a wired connection, a wireless connection, or a physical memory device. Selected panels 346 from the menu 344 to pair with the specimen are displayed adjacent to the specimen identifier 342. In other examples, one or more panels to be paired with the specimen are automatically assigned by the LIS, and the appropriate panels are automatically populated as the selected panels 346.

If one or more of the selected panels 346 requires a white blood cell concentration estimate of the specimen to be obtained prior to sample processing (e.g., because a sample volume of the specimen to be prepared is dependent on the white blood cell concentration), the user interface 340 includes two additional options for selection. A first option 348 can be selected when the cell concentration estimator 106 of the sample preparation instrument 100 is to estimate the white blood cell concentration internally. A second option 350 can be selected when an external source has already determined the white blood cell concentration. The white blood cell concentration can be manually entered into a text box 352 of the user interface 340 when the second option 350 has been selected. Alternatively, the white blood cell concentration can be automatically populated within the text box 352 if the white blood cell concentration is received and downloaded from the LIS. In some examples, the user can accept or reject the automatically populated value.

This process can be repeated for each tube within the input cassette. For example, the machine-readable code of each of the tubes comprising a specimen within the input cassette can be scanned to retrieve the specimen identifiers associated with the respective specimens. These specimen identifiers 354 can be displayed within the user interface 340. Selected panels 356 assigned to the specimen identifiers 354 can be displayed adjacent to respective specimen identifiers 354. The selected panels 356, similar to the selected panels 346 can be selected from a menu similar to the menu 344 or automatically populated by the LIS. Additionally, for each of the selected panels 356 that require the white blood cell concentration for the specimen to be determined, either the first option 348 or the second option 350 is selected.

Once the user has assigned panels to each of the specimen tubes in the input cassette and the first option 348 or second option 350 has been selected for each applicable panel, the user can select a load control 358 displayed in the user interface 340. Upon selection of the load control 358, the input cassette is now moved into the input station 124 of the sample preparation instrument 100 and is ready for processing.

Figure 14:
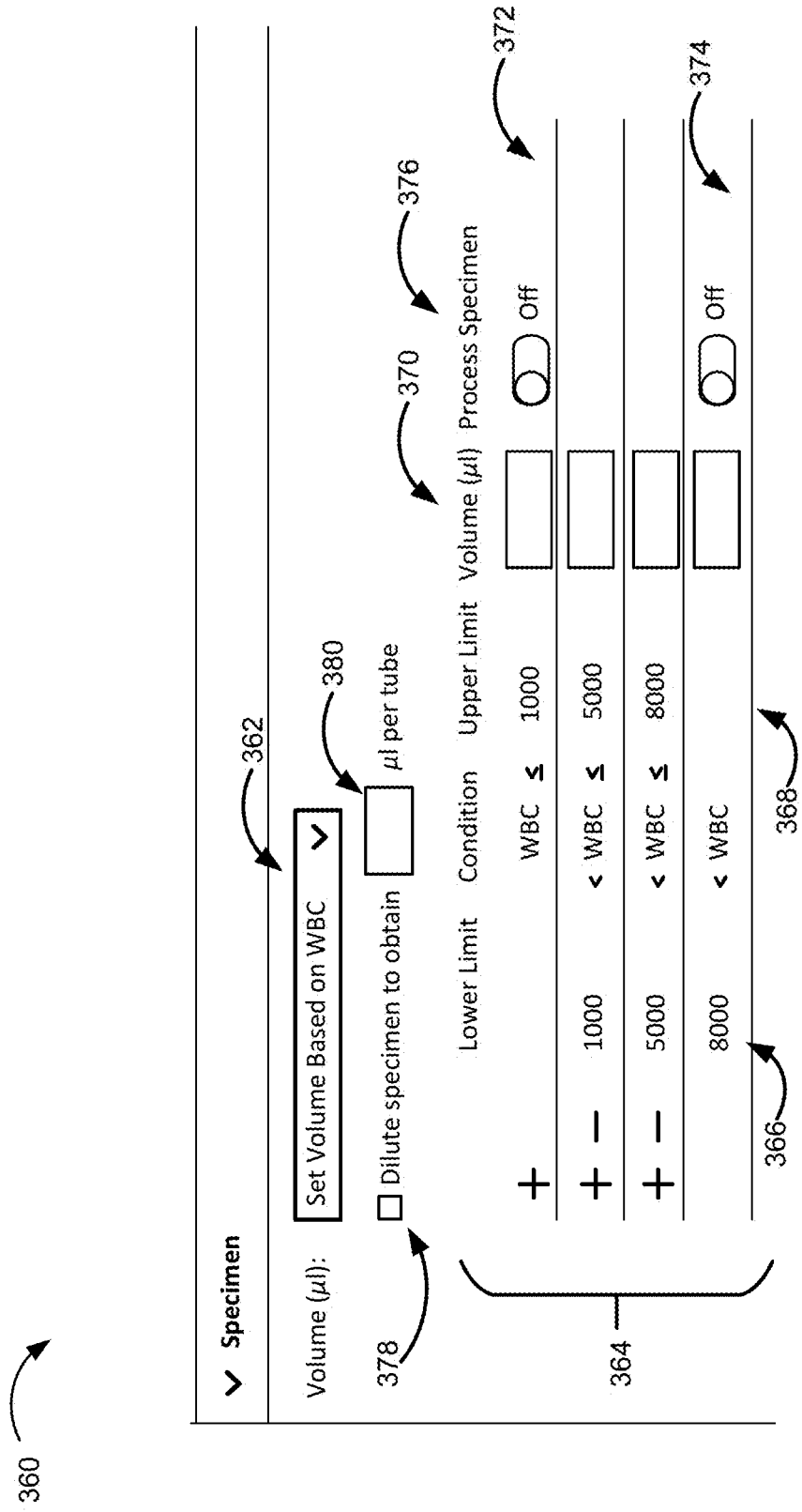
FIG. 14 is an example user interface for receiving a set of predefined rules for preparing a specimen for analysis.

FIG. 14 is an example user interface 360 of a panel authoring and management application. In some examples, the panel authoring and management application can be executed on a remote computing device that is separate from the sample preparation instrument 100. The user interface 360 can receive a set of predefined rules as input for preparing a particular type of specimen for a particular type of analysis. A panel can be defined or created based on the predefined rules, and transmitted to the sample preparation instrument 100 over a wired connection, a wireless connection, or a physical memory device for storage. The panel can then be displayed within the user interface 340 of the touch display 122 of the sample preparation instrument 100 for selection by the user (e.g., within the menu 344 for pairing with a specimen) as discussed in detail above with reference to FIG. 13. In other examples, the panel authoring and management application can be executed on the sample preparation instrument 100 and the user interface 360 displayed on the touch display 122.

As one example, a user creating the panel can input the set of predefined rules for sample preparation via the user interface 360. In some examples, the set of predefined rules can be specific to a type of specimen and/or a type of analysis to be performed on the specimen. As illustrated, the user interface 360 is provided to facilitate input of predefined rules associated with a sample volume of the specimen to be included within the sample. The user interface 360 can also facilitate input of other types of predefined rules, including labeling reagent volumes, lytic reagent volumes, incubation time periods, and other similar rules.

For receiving rules associated with the sample volume of the specimen, the user interface 360 includes a menu 362 to select a basis for setting the sample volume of the specimen. One example basis can include setting the sample volume of the specimen based on a white blood cell concentration in the specimen. This basis can be selected for a panel that analyzes subsets of white blood cells, such as a leukemia or lymphoma panel, for example. Another example basis can include setting a fixed volume.

Upon a selection to set the sample volume of the specimen based on the white blood cell concentration in the specimen, the user interface 360 can display a table 364. A range of white blood cell concentration values and a corresponding sample volume can be input into each row of the table 364. For example, each range can have a lower limit concentration value 366, an upper limit concentration value 368 and a corresponding sample volume 370. In some examples, one row of the table 364 (e.g., row 372) represents a minimum white blood cell concentration value rather than a range, and another row of the table 364 (e.g., row 374) represents a maximum white blood cell concentration value rather than a range. For these rows representing maximum and minimum values, a processing option 376 can be provided. For example, using the processing option 376, the user can define whether the specimen is to be processed based on the estimated white blood cell concentration in the specimen (e.g., the user can define rules used in decision 328 and operation 332). As one example, the specimen is not processed when the white blood cell concentration is at or above the maximum concentration value or when the white blood cell concentration is at or below the minimum concentration value.

Additionally, the user interface 360 provides a dilution option 378 and a particular sample volume 380 to inform an amount of diluent to be added to reach the sample volume 380. For example, the user interface 360 enables the user to define the rules used in decision 334 and operation 336 regarding whether to dilute the sample volume of the specimen in order to maintain a specified volume of specimen for labeling that has been defined for the panel.

Figure 15:
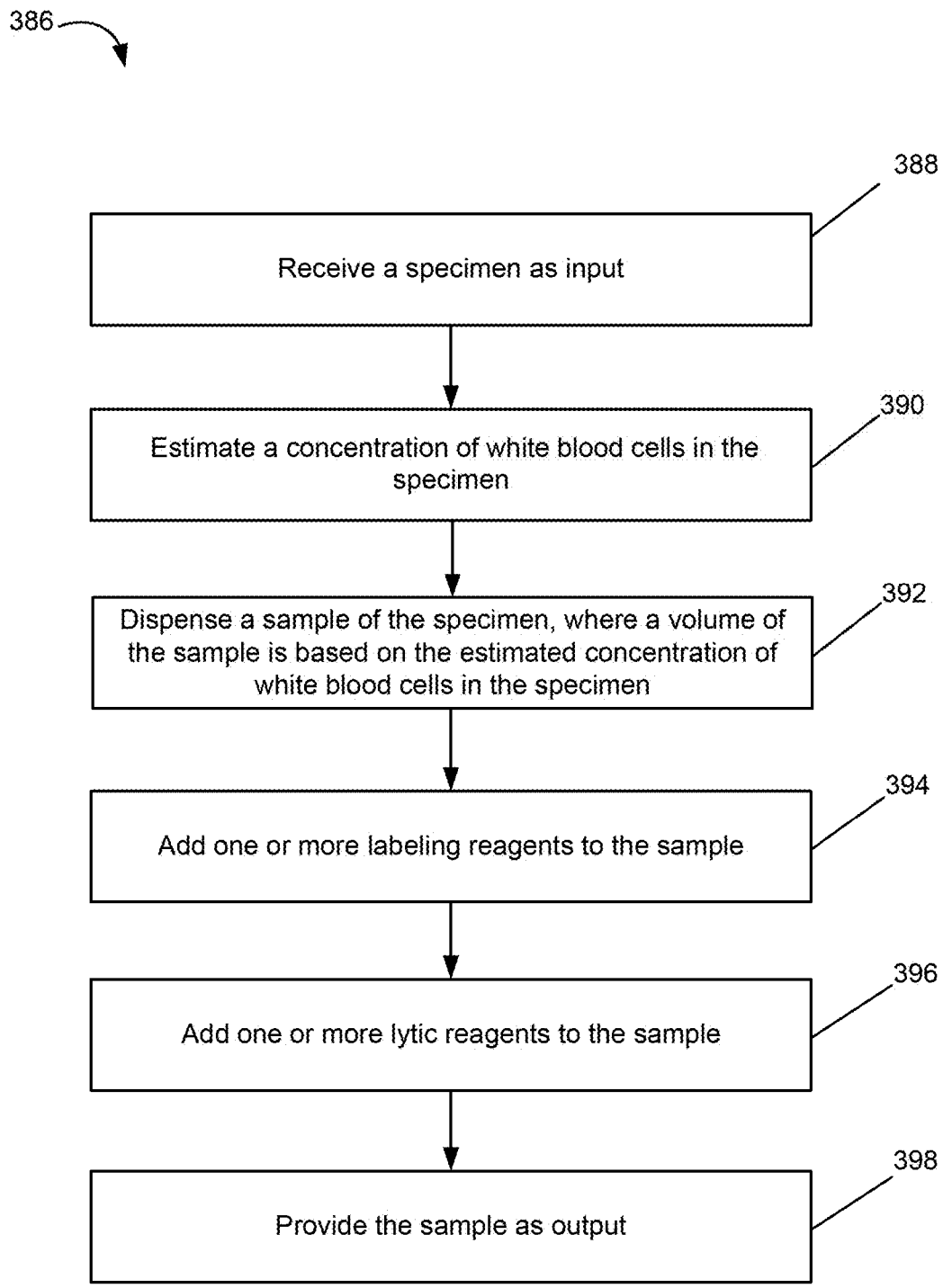
FIG. 15 is a flowchart illustrating a method for preparing a sample of a specimen for analysis.

FIG. 15 is a flowchart illustrating a method 386 for preparing a sample for analysis. The method 386 is performed by the sample preparation instrument 100. At operation 388, a specimen is received as the input 102 to the sample preparation instrument 100. The specimen is to be prepared for analysis by a sample analyzer, for example. Example specimens can include whole blood, bone marrow, dissociated tissues, peripheral mononuclear cells, fine needle aspirates, cerebrospinal fluid, and other single cell-suspensions. As one example, the specimen is whole blood that is being prepared for a leukemia or lymphoma panel to analyze a subset of white blood cells.

At operation 390, a concentration of white blood cells in an aliquot of the specimen is estimated, which is representative of the concentration of white blood cells in the specimen. The concentration can be determined using an optical method, an electrical resistance method, or a flow cytometry method, among other methods. At operation 392, a sample of the specimen is dispensed, where a volume of the sample (e.g., also referred to as the "sample volume of the specimen") can be determined based on the estimate and a set of predefined rules associated with the particular type of analysis (e.g., the panel) that the specimen is being prepared for. The set of predefined rules can include a minimum white blood cell concentration value, a maximum white blood cell concentration value, and one or more ranges of white blood cell concentration values between the minimum and maximum values, where each range has a corresponding sample volume of the specimen. Therefore, the determined sample volume of the specimen is the sample volume that corresponds to a range concentration values into which the estimate of the white blood cell concentration falls.

To process the sample at least operations 394 and 396 are performed. At operation 394, one or more labeling reagents are added to the sample (e.g., added to the sample volume of the specimen). The sample volume of the specimen and the labeling reagents can then be incubated for a predetermined time period. The labeling agents target a particular constituent of the specimen to facilitate analysis. For example, continuing the above example, the labeling reagents can include antibody reagents that target a subset of white blood cells (e.g., attach to the subset of white blood cells during the incubation period) to facilitate analysis of the subset of the white blood cells during the leukemia or lymphoma panel.

At operation 396, one or more lytic reagents are added to the sample (e.g., added to the sample volume of the specimen). The sample volume of the specimen and the lytic reagents can then be incubated for a predetermined time period. Continuing the above example, the lytic reagents can destroy red blood cells within the sample volume of the specimen. In other examples, buffers rather than or in addition to the lytic reagents can be added to sample volume of the specimen. At operation 398, the sample is provided as the output 104 of the sample preparation instrument 100, and the method 386 ends.

Figure 16:
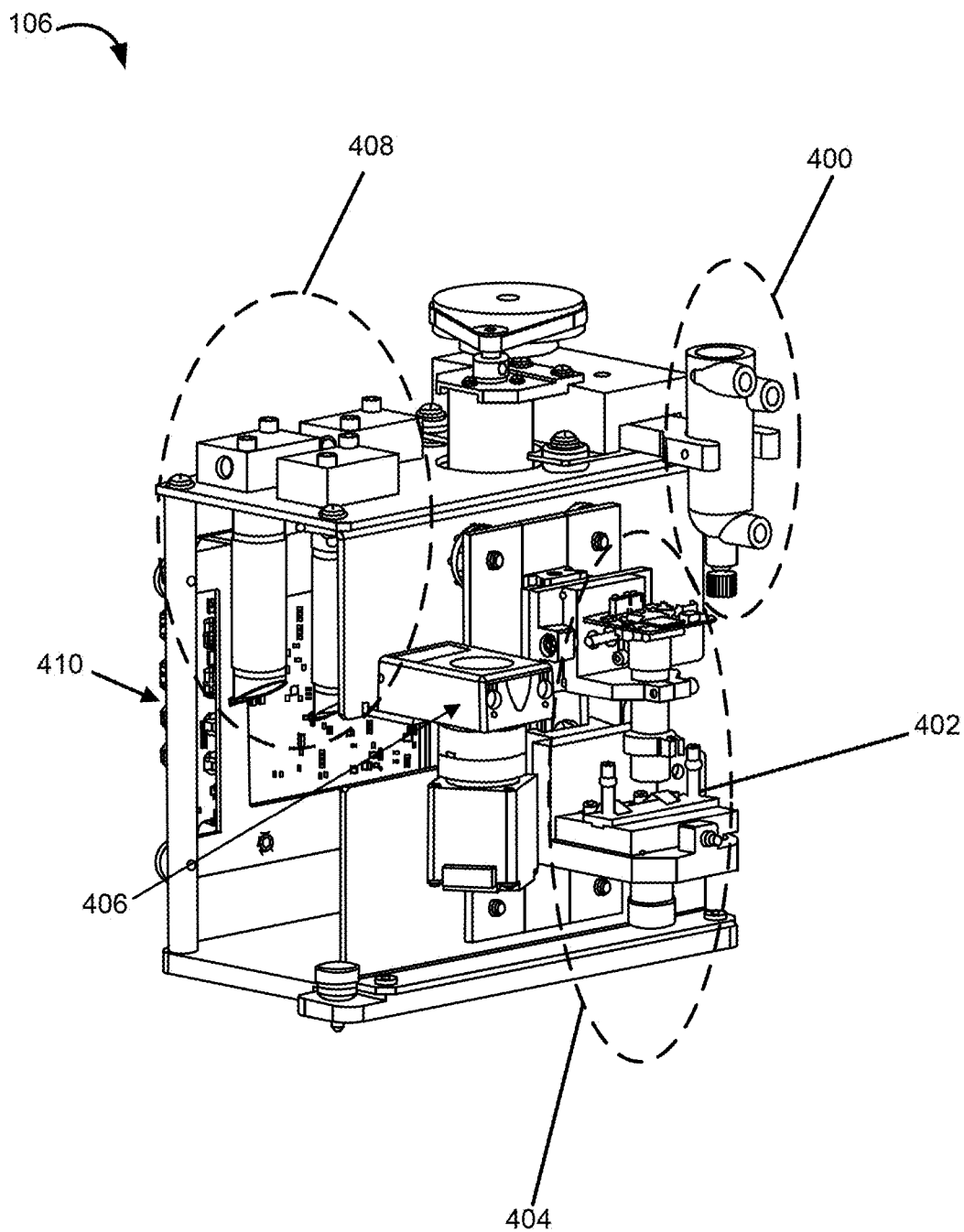
FIG. 16 illustrates hardware components of an example cell concentration estimator.

FIG. 16 illustrates hardware components of an example cell concentration estimator 106. The cell concentration estimator 106 is a component of the sample preparation instrument 100. In some examples, the cell concentration estimator 106 can be detachable from the sample preparation instrument 100 for servicing. This particular configuration of the cell concentration estimator 106 can implement an optical method to estimate a concentration of white blood cells in a specimen.

The cell concentration estimator 106 includes a mixing chamber 400, a counting chamber 402, an optical system 404 arranged relative to the counting chamber 402, a fluidic pump 406, a plurality of reagent pumps 408, and one or more electronic boards 410. The mixing chamber 400 receives and mixes a lytic reagent and diluent reagent with an aliquot of the specimen using a motor of the mixing chamber 400. The lysed and diluted aliquot of the specimen is advanced from the mixing chamber 400 to the counting chamber 402 by the fluidic pump 406. As the lysed and diluted aliquot of the specimen is advanced through the counting chamber 402, the optical system 404 captures images of the specimen. The electronic boards 410 supply power and signals to the motor of the mixing chamber 400, the fluidic pump 406, and the plurality of reagent pumps 408. The computing device 116 of the sample preparation instrument 100 provides the signals to the electronic boards 410 to control a timing, a rate, and/or a pattern of mixing performed by the motor, a timing and an amount of volume of reagents pushed by each of the reagent pumps 408, as well as a timing and amount of volume pushed by the fluidic pump 406.

Figure 17:
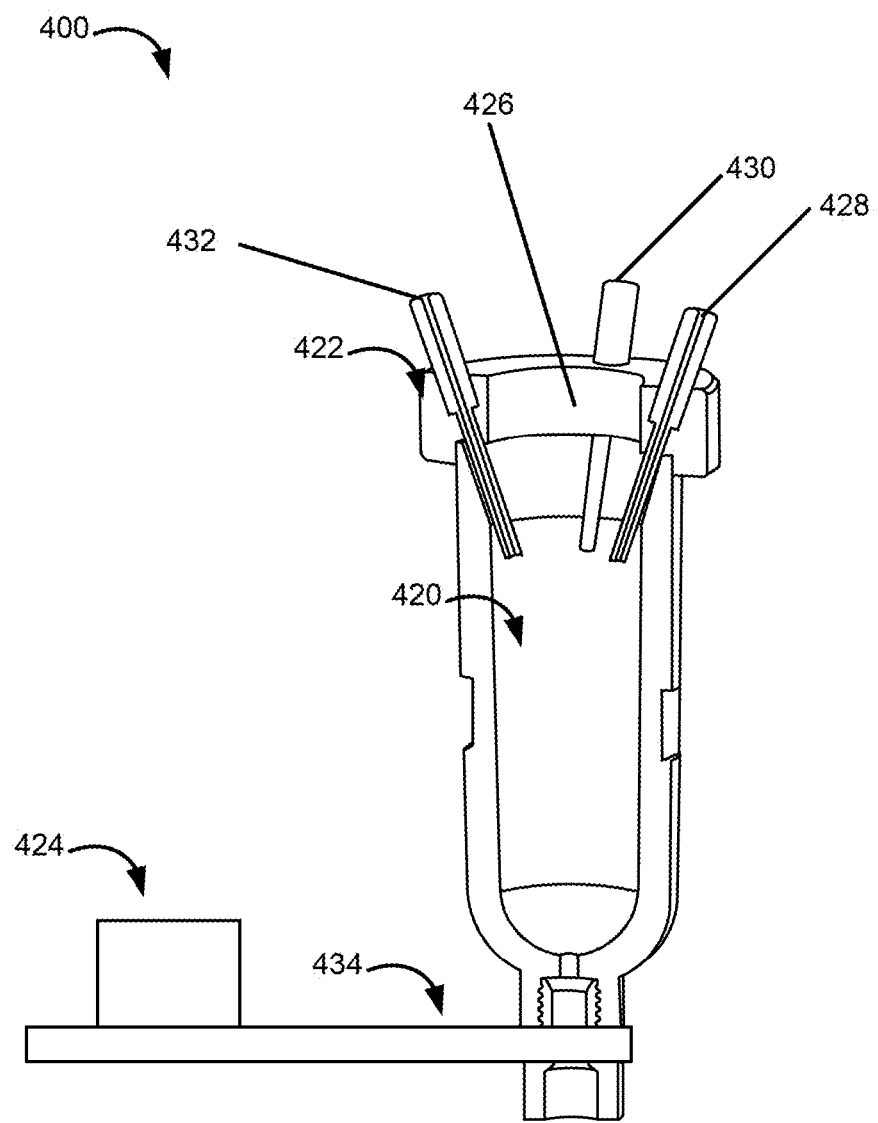
FIG. 17 is an example mixing chamber of a cell concentration estimator.

FIG. 17 is an example mixing chamber 400 of a cell concentration estimator 106. The mixing chamber 400 comprises a vessel 420, a cap 422 positioned on an open end of the vessel 420, and a motor 424. The vessel 420 holds the aliquot of the specimen and one or more reagents that are received for mixing with the aliquot and/or for cleaning the cell concentration estimator 106 after obtaining a white blood cell concentration. As one non-limiting example, the maximum functional volume of the vessel 420 is 6.0 milliliters (mL).

The cap 422 includes an opening 426 to receive the probe 114 of the transfer station 112, the probe 114 aspirating and transferring the aliquot of the specimen from a tube comprising the specimen at the input station 124 or the single tube loader 126 to the vessel 420. The cap 422 also includes a plurality of input ports 428, 430, and 432 to receive one or more of a lysing reagent, a diluent reagent, and a cleaning reagent via one or more of a first line, a second line, and a third line. The reagents can be pushed through the lines into the vessel 420 using the reagent pumps 408. The lines entering into the vessel 420 can be positioned for angular dispensing to a center bottom section of the vessel 420. In some examples, a position of the cap 422 is set during manufacturing and is stationary during operation of the mixing chamber 400.

The motor 424 is configured to mix the contents of the mixing chamber 400. In some examples, the motor 424 is fitted with an eccentric and an arm 434 attached to the center of the mixing chamber 400.

Figure 18:
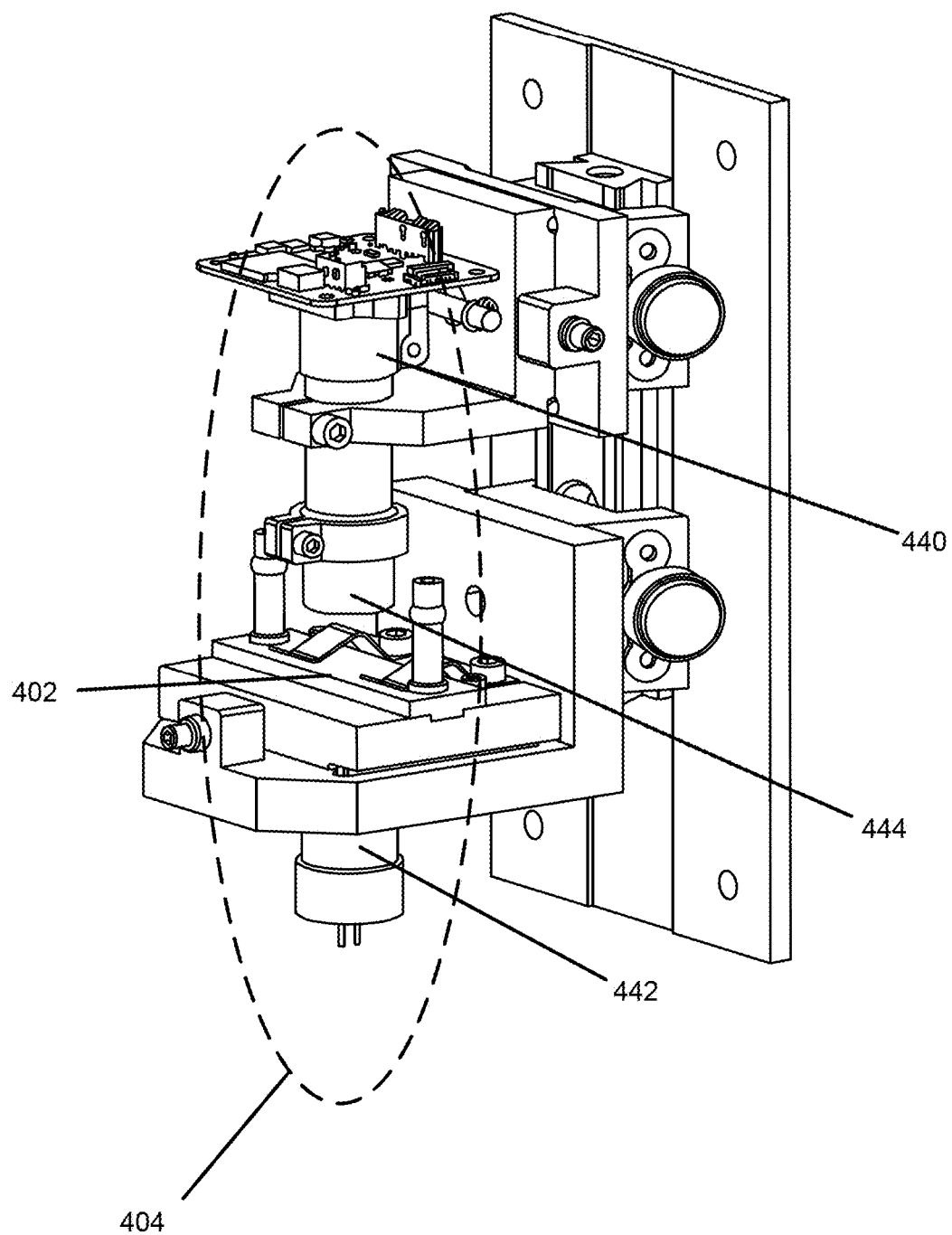
FIG. 18 is an example counting chamber and optical system of a cell concentration estimator.

FIG. 18 is an example counting chamber 402 and optical system 404 of a cell concentration estimator 106. The optical system 404 can be arranged and/or positioned relative to the counting chamber 402. In some examples, the counting chamber 402 is a flow cell chamber comprised of one or more transparent flow cells. An entrance port of the counting chamber 402 can be connected to the mixing chamber 400 via a first portion of pump tubing. An exit port of the counting chamber 402 can be connected to the fluidic pump 406 via a second portion of pump tubing. The fluidic pump 406 can advance at least a portion of the lysed and diluted aliquot of the specimen from the mixing chamber 400 through the first portion of pump tubing to the entrance port of the counting chamber 402, continue to advance the aliquot through the counting chamber 402, out of the exit port, and through the second portion of pump tubing to be dispensed in a waste container, such as the waste container 142. As the aliquot of the specimen is advanced by the fluidic pump 406 through the counting chamber 402 (e.g., as cells move through the flow cell), the optical system 404 captures a plurality of images. In some examples, the fluidic pump 406 temporarily stops advancing the aliquot such that the optical system 404 can capture images while the cells of the specimen have stopped moving within the counting chamber 402. The fluidic pump 406 can then restart until a next temporary stop, and this process continues until each image has been captured. As one non-limiting example, the fluidic pump 406 can be set at 10 µL per push in order to for images to be captured by the optical system 404 at a rate of 0.6 seconds per image.

The optical system 404 includes a digital camera 440, a light source 442, and a lens 444. In some examples, the optical system 404 implements a bright field imaging and illumination technique, where the sample is illuminated from below by the light source 442 and imaged from above by the camera 440. Sample illumination can be transmitted blue light, and contrast in the sample can be caused by the attenuation of the transmitted light in a circular area of the sample. The lens 444 is used to image the cells into the camera 440. The camera 440 is communicatively connected to the computing device 116 of the sample preparation instrument 100 to facilitate transmission of the captured and digitized images to the computing device 116 for processing and analysis.

In other examples, the optical system 404 implements fluorescence microscopy, and includes a fluorescence microscope coupled with a digital camera similar to camera 440 that is communicatively connected to the computing device 116 of the sample preparation instrument 100 to facilitate transmission of the captured and digitized images to the computing device 116 for processing and analysis.

Figure 19:
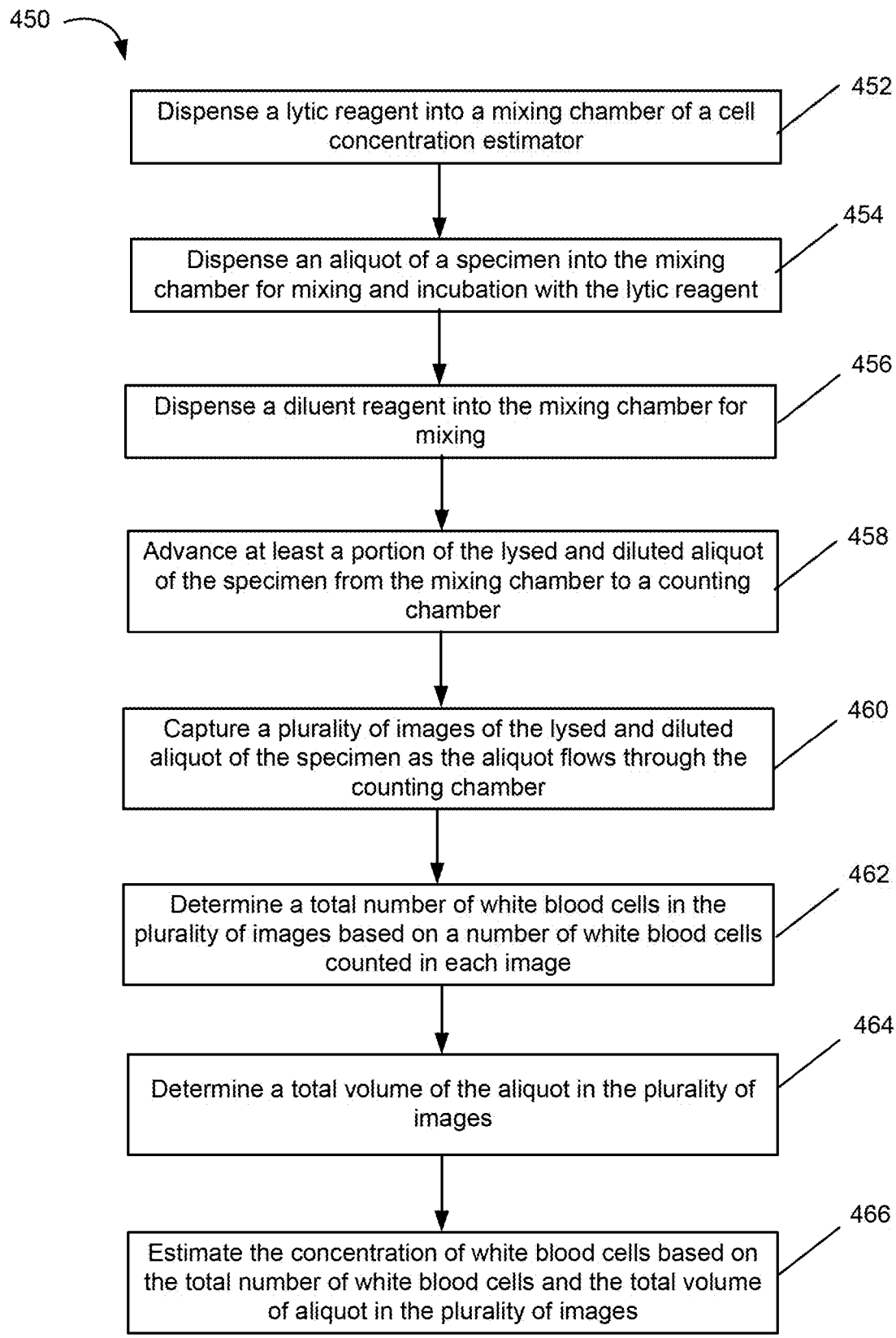
FIG. 19 is a flowchart illustrating an optical method for estimating a white blood cell concentration in a specimen.

FIG. 19 is a flowchart illustrating an optical method 450 for estimating a white blood cell concentration in a specimen. The optical method 450 is performed by the cell concentration estimator 106 of the sample preparation instrument 100 described in detail in FIGS. 16, 17, and 18.

The method begins at operation 452, where a lytic reagent is dispensed into the mixing chamber 400. An aliquot of the specimen is then dispensed into the mixing chamber 400 at operation 454 for mixing and incubation with the lytic reagent for a predetermined time period. When the specimen is whole blood, the lytic reagent lyses red blood cells within the sample. For example, the lytic reagent causes membrane disorganization and breakdown of the red blood cells, leaving red blood cell debris.

After the predetermined time period for incubation of the aliquot of the specimen and the lytic reagent expires, a diluent reagent is dispensed into the mixing chamber 400 at operation 456 to be mixed with the aliquot of the specimen and the lytic agent. The diluent reagent slows down the lytic activity to prevent the destruction of white blood cells, as well as dilutes the sample to facilitate a counting of the white blood cells. At operation 458, the fluidic pump 406 advances at least a portion of the lysed and diluted aliquot of the specimen from the mixing chamber 400 to the counting chamber 402.

At operation 460, a plurality of images of the lysed and diluted aliquot of the specimen are captured by the optical system 404 as the aliquot flows through the counting chamber 402. For example, once the counting chamber 402 is filled with the aliquot, the fluidic pump 406 temporarily stops transferring fluid causing the white blood cells in the specimen to stop moving. While the movement of the white blood cells is temporarily stopped, the optical system 404 captures and digitizes an image. Once the image is captured and digitized, the fluidic pump 406 will again advance the sample and then stop to capture another image. This process is repeated to capture the plurality of images. For example, the process can be repeated until a sufficient number of images have been captured to provide a statistically significant estimate of a number of white blood cells.

The plurality of images are then transferred to the computing device 116 of the sample preparation instrument 100 for image processing and analysis. For example, at operation 462, a total number of white blood cells in the plurality of images is determined based on a number of white blood cells counted in each image. At operation 464, a total volume of the aliquot in the plurality of images is determined. For example, as described in greater detail in FIG. 21, during a manufacturing setup of the sample preparation instrument 100, an image of a stage micrometer captured by the optical system 404 is received, and a horizontal length and a vertical length of the image are measured. An image volume can be determined based on the horizontal length, the vertical length, and a known path length of a flow cell in the counting chamber 402. The image volume can be stored at the computing device 116. The total volume of the aliquot in the plurality of images can then be determined based on the image volume and a number of images in the plurality of images. At operation 466, the concentration of white blood cells is estimated based on the total number of white blood cells and the total volume of the aliquot in the plurality of images.

Figure 20:
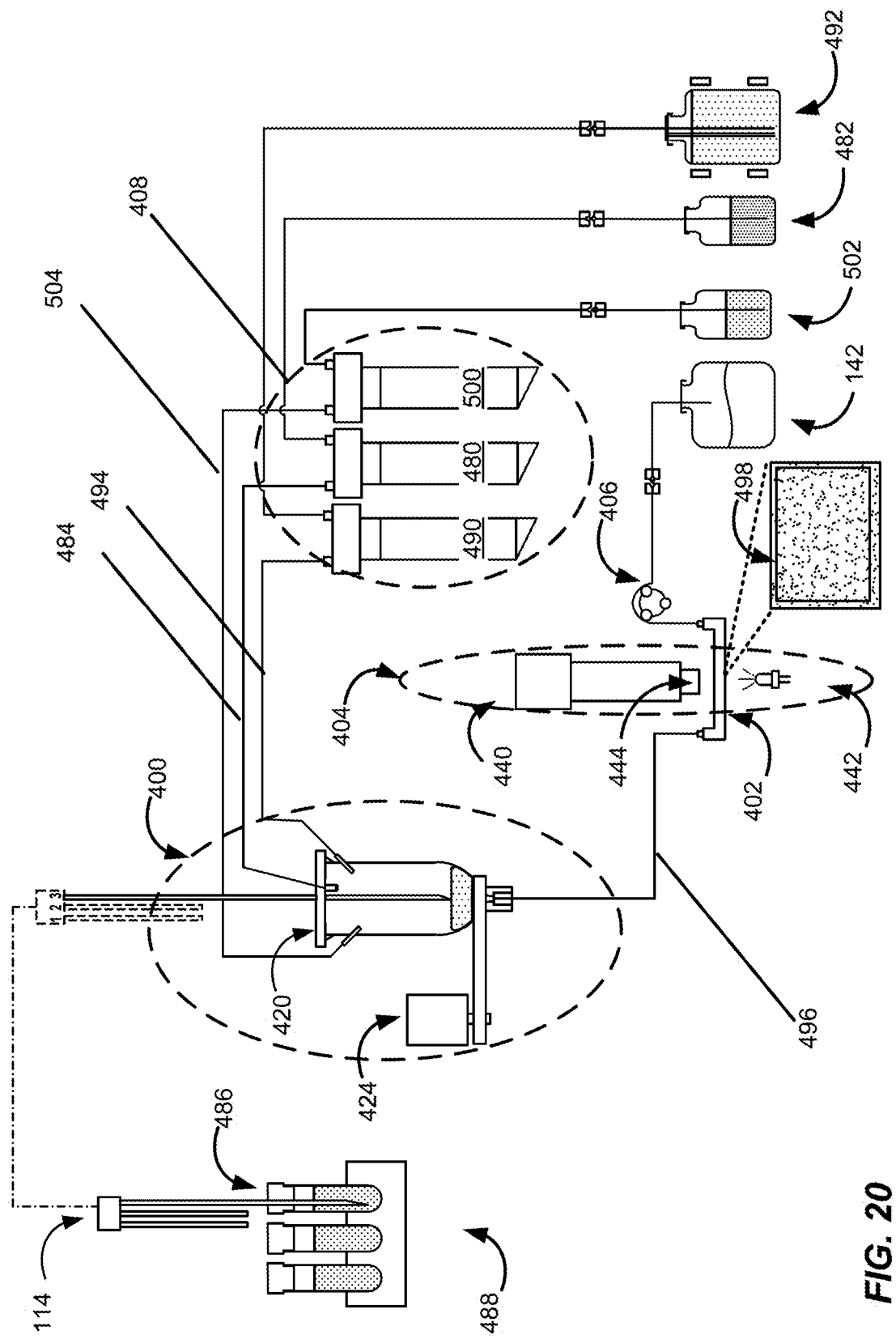
FIG. 20 schematically illustrates an optical method for estimating a white blood cell concentration in a specimen.

FIG. 20 schematically illustrates an example optical method for estimating a white blood cell concentration for a specimen. The optical method illustrated can be similar to the optical method 450 described in FIG. 19 performed by the cell concentration estimator 106 of the sample preparation instrument 100. For example, a lytic reagent pump 480 of the reagent pumps 408 aspirates a lytic reagent from a container 482 comprising the lytic reagent. The lytic reagent pump 480 pushes the lytic reagent through a first line 484 to dispense the lytic reagent via one of the input ports (e.g., input port 428) into the vessel 420 of the mixing chamber 400. In one example, a 250 µL volume of the lytic reagent is dispensed into the vessel 420.

The probe 114 of the transfer station 112 can then pierce a capped tube 486 comprising the specimen that is held within an input cassette 488 at the input station 124, for example. The probe 114 can aspirate, transport, and then dispense an aliquot of the specimen into the vessel 420 of the mixing chamber 400. In one example, a 10 µL to 50 µL volume of the specimen is dispensed into the vessel 420. A motor 424 of the mixing chamber 400 can be activated to provide a mechanical mixing of the aliquot of the specimen and the lytic reagent. The aliquot of the specimen and the lytic reagent are mixed and allowed to incubate for a predetermined time period. As one example, the aliquot of the specimen and the lytic reagent can be mixed for 15 seconds in a circular or elliptical pattern. The mixing action then stops and waits to incubate for an additional 9 seconds. Thereafter, mixing is resumed for an additional 9 seconds, and then stopped again to rest and incubate for an additional 9 seconds. Incubation is finalized with 3 seconds of mixing.

A diluent reagent pump 490 of the reagent pumps 408 can then aspirate a diluent reagent from a container 492 comprising the diluent reagent. The diluent reagent pump 490 pushes the diluent reagent through a second line 494 to dispense the diluent reagent via another one of the input ports (e.g., input port 430) into the vessel 420 of the mixing chamber 400. In some examples, the diluent reagent is further used by other components of the sample preparation instrument 100 during the processing of the sample. The motor 424 of the mixing chamber 400 can again be activated to provide a mechanical mixing of the aliquot of the specimen, lytic agent, and the diluent agent. In one example, a 900 µL volume of diluent reagent is dispensed and 3 second of mixing proceeds.

A fluidic pump 406 advances at least a portion of the lysed and diluted aliquot of the specimen from the mixing chamber 400 to the counting chamber 402 through a first portion of a pump tubing 496. In one example, about 600 µL of the diluted and lysed aliquot of the specimen is primed through the pump tubing 496 by the fluidic pump 406. After the counting chamber 402 has been primed with the diluted and lysed aliquot of the specimen, the fluidic pump 406 temporarily stops advancing the aliquot causing the white blood cells in the specimen to stop moving. While the movement of the white blood cells is temporarily stopped, the optical system 404 comprised of the camera 440, a light source 442, and the lens 444 captures and digitizes an image 498. Once the image 498 is captured and digitized, the fluidic pump 406 will begin to advance the aliquot again and then stop to capture another image. This process is repeated to capture a plurality of images. As one non-limiting example, images may be captured every 0.6 sec until 50 images are captured. However, some aliquots may require up to 1000 images to be captured. The plurality of images are provided to the computing device 116 for processing and analysis to estimate a white blood cell concentration in the specimen.

The fluidic pump 406 advances the aliquot through the counting chamber 402 to the waste container 142 via the second portion of the pump tubing 496 for disposal, such as the waste container 142. Once the plurality of images are captured, remaining lysed and diluted aliquot of the specimen in the vessel 420 of the mixing chamber 400, if any, can be advanced through the counting chamber 402 to the waste container 142. In some examples, a cleaning reagent pump 500 of the reagent pumps 408 aspirates a cleaning reagent from a container 502 comprising the cleaning reagent through a third line 504 to dispense into the vessel 420 of the mixing chamber 400. The cleaning reagent is then advanced by the fluidic pump 406 from the mixing chamber 400 to the counting chamber 402 via the first portion of the pump tubing 496, and then from the counting chamber 402 to the waste container 142 via the second portion of the pump tubing 496 to clean out each component of the cell concentration estimator 106 in preparation for a next aliquot of specimen to be received.

Figure 21:
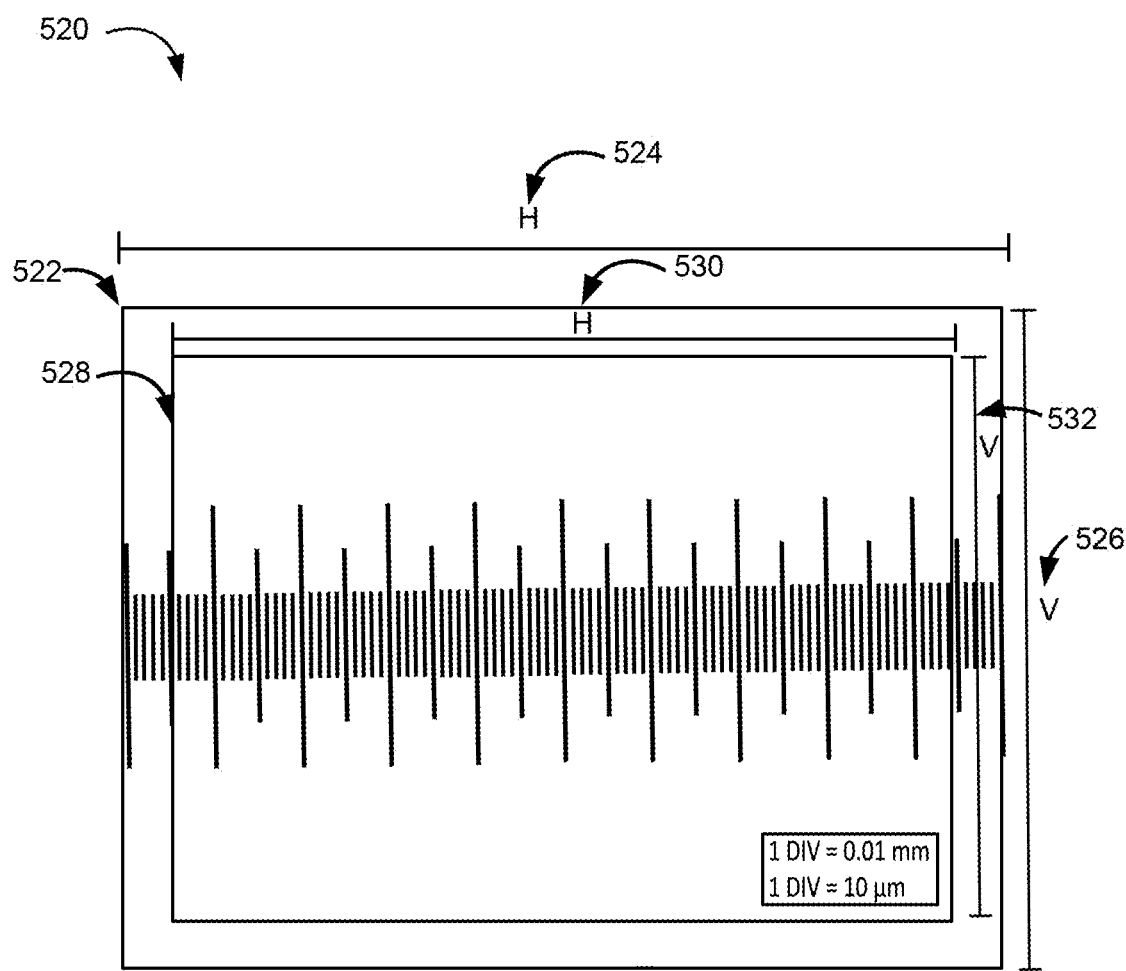
FIG. 21 illustrates an image of a stage micrometer used to determine a total volume in a plurality of captured images.

FIG. 21 illustrates an image of a stage micrometer used to determine a total aliquot volume in a plurality of captured images. During a manufacturing setup of the sample preparation instrument 100, an image 520 of a stage micrometer (e.g., an image of a slide having a scale on its surface) can be captured, and horizontal and vertical lengths and image volumes associated with views of the image 520 can be determined. The determined lengths and/or image volumes can then be transmitted to the computing device 116 for storage and use in determining the total aliquot volume.

In some examples, a full field of view can be measured from the image 520, hereinafter referred to as a full view 522. For example, a horizontal length 524 and vertical length 526 of the full view 522 are measured to determine an area of the full view 522. A depth of the full view 522 is based on known measurements associated with the counting chamber 402. For example, a known path length of the flow cell in the counting chamber 402. The area and depth are then multiplied to achieve a full image volume for the full view 522. The full image volume can be stored at the computing device 116 of the sample preparation instrument 100.

As one non-limiting example, the digital camera 440 can use a ⅓" format having 1280×960 pixels and a pixel size of 3.75 mm in the horizontal direction by 3.75 mm in the vertical direction resulting in a full image area of 4800 (e.g., full image format 1280*pixel size 3.75). The measured full image length is 1 mm for the horizontal length 524 and 0.750 mm for the vertical length 526, resulting in a full view image area of 0.75 mm$^2$. The path length of the flow cell is 0.0853 mm, and thus the full image volume is 0.75 mm$^2$×0.0853 mm or 0.064 mm$^3$.

Once the plurality of images are captured by the optical system 404, a total aliquot volume in the plurality of images captured can be determined by the computing device 116 based on the full image volume. For example, the full image volume is converted to μL (e.g., 1 mm$^3$=1 μL) and multiplied by a number of images in the plurality of images captured to obtain a total aliquot volume in the plurality of images. For example, if 50 images were captured and the full image volume of 0.064 mm$^3$ was determined, then a total aliquot volume in the plurality of images would be 3.200 μL.

To obtain the estimate of the white blood cell concentration, a number of white blood cells counted in each image are added together to get a total number of white blood cells in the plurality of images. The total number of white blood cells in the plurality of images is then divided by the total aliquot volume in the plurality of images to obtain the estimate of the white blood cell concentration (a number of white blood cells per μL).

Additionally, in some examples, to avoid problems with identifying and counting white blood cells that are on an edge of the full view 522 of the digital camera 440, a counting border is introduced on at least two sides of the image 520. The border effectively reduces a number of pixels in the field of view. Therefore, a field of view inside the counting border can be measured from the image of the stage micrometer, hereinafter referred to as an effective view 528. Continuing the above example, a counting border set at 50 μm may reduce the image to 1134×814 pixels resulting in an effective image area of 3600 microns (e.g., full image format 1134*pixel size 3.75). The measured effective image length is 0.889 mm for the horizontal length 530 and 0.639 mm for the vertical length 532, resulting in an effective image are of 0.568 mm$^2$. Thus, the effective image volume is 0.568 mm$^2$×0.0853 mm or 0.0485 mm$^3$.

The effective image volume can be stored at the computing device 116 of the sample preparation instrument 100 to allow the computing device 116 to determine a total aliquot volume in the plurality of images captured by the optical system 404. For example, the effective image volume is converted to μL (e.g., 1 mm$^3$=1 μL) and multiplied by a number of images in the plurality of images captured to obtain a total aliquot volume in the plurality of images. Accordingly, if 50 images were captured and the effective image volume of 0.0485 mm$^3$ was determined, then total aliquot volume in the plurality of images would be 2.4250 μL. To obtain the estimate of the white blood cell concentration, a number of white blood cells counted in each image (e.g., counted within the border of the image) are added together to get a total number of white blood cells in the plurality of images. The total number of white blood cells in the plurality of images is then divided by the total aliquot volume in the plurality of images to obtain the estimate of the white blood cell concentration (a number of white blood cells per μL).

Figure 22:
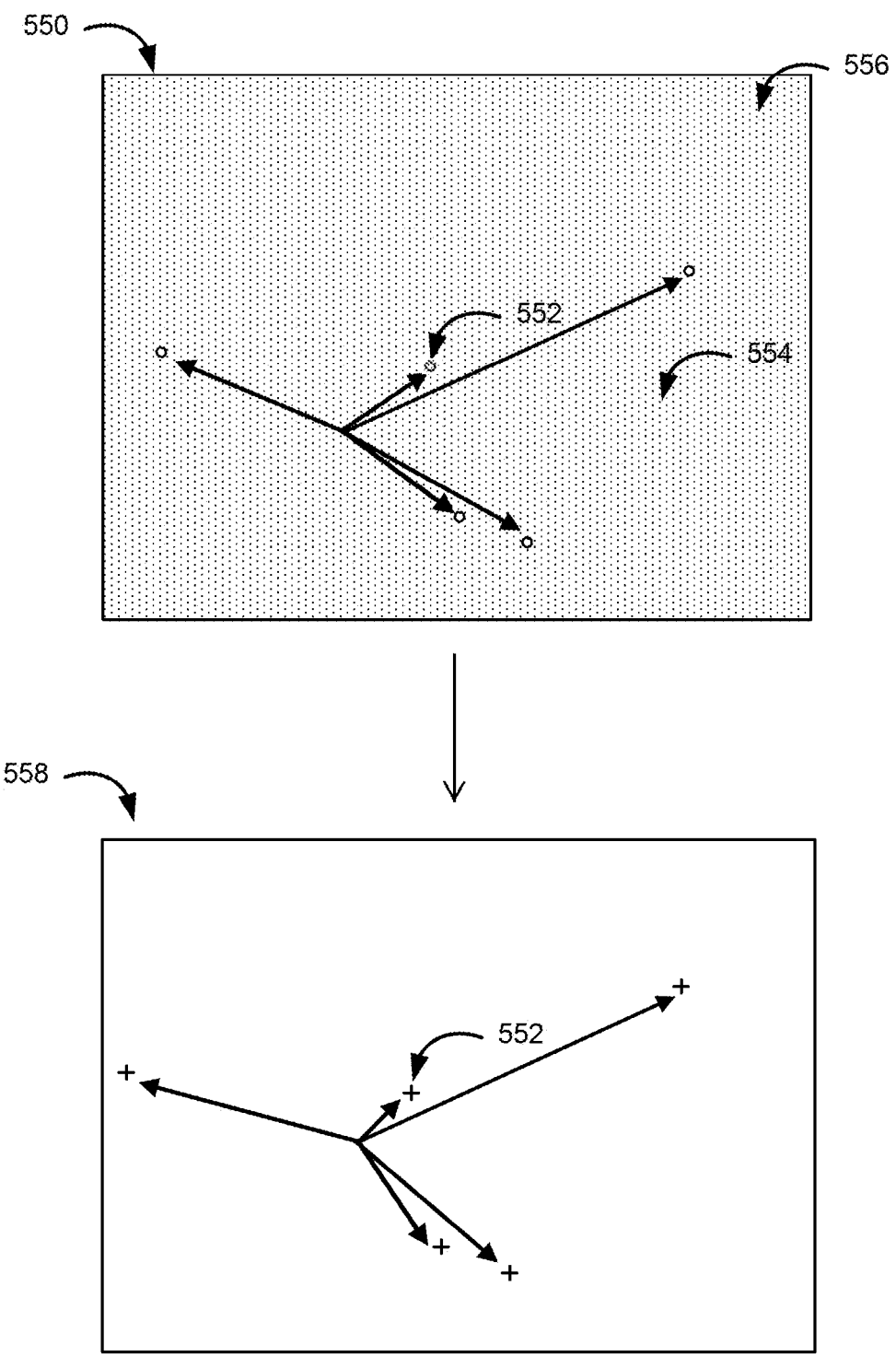
FIG. 22 illustrates an image analysis performed to determine a number of white blood cells in an image.

FIG. 22 illustrates an image analysis performed to determine a number of white blood cells in an image. The image analysis can be performed by the computing device 116 of the sample preparation instrument 100. For example, the computing device 116 may be communicatively coupled to the optical system 404 of the cell concentration estimator 106, and receive the plurality of images of the sample captured by the optical system 404. In some examples, the computing device 116 and the optical system 404 can communicate over a wireless connection. In other examples, the computing device 116 and the optical system 404 can communicate over a wired connection.

The processing device 120 of the computing device 116 can analyze each image individually. When received, the image is in a raw image data format (e.g., raw image 550) that includes the white blood cells 552, debris 554, and a background 556. The debris 554 can include red blood cell debris resulting from the mixing with the lytic reagent, among other debris. To increase contrast and facilitate the counting of a number of the white blood cells 552, the background 556 can be subtracted to generate a subtracted image 558. For example, by subtracting the background 556 distinguishing between the white blood cells 552 and the debris 554 can become easier. In some examples, one or more of the white blood cells 552 or an area in the subtracted image 558 can be hovered over or selected to confirm whether each of the white blood cells 552 was analyzed (e.g., counted as a white blood cell). For example, when a white blood cell has been analyzed and counted, and the white blood cell or the area comprising the white blood cell is hovered over or selected, a symbol such as a cross can be displayed to indicate the cell was counted. In some examples, this function and display can be internal to the computing device 116 performing the image analysis and not displayed to the user of the sample preparation instrument 100.

The computing device 116 can determine a variety of different values, including a white blood cell count for each image, an average white blood cell count per image, and a cumulative white blood cell count for the plurality of images (e.g., a summation of the white blood cell counts for each image). Additionally, as part of the image analysis process the computing device 116 can determine a total aliquot volume in the plurality of images, as described in detail above in FIG. 21. Therefore, the computing device 116 can estimate the concentration of white blood cells based on the total white blood cell count and the total aliquot volume in the plurality of images.

Figure 23:
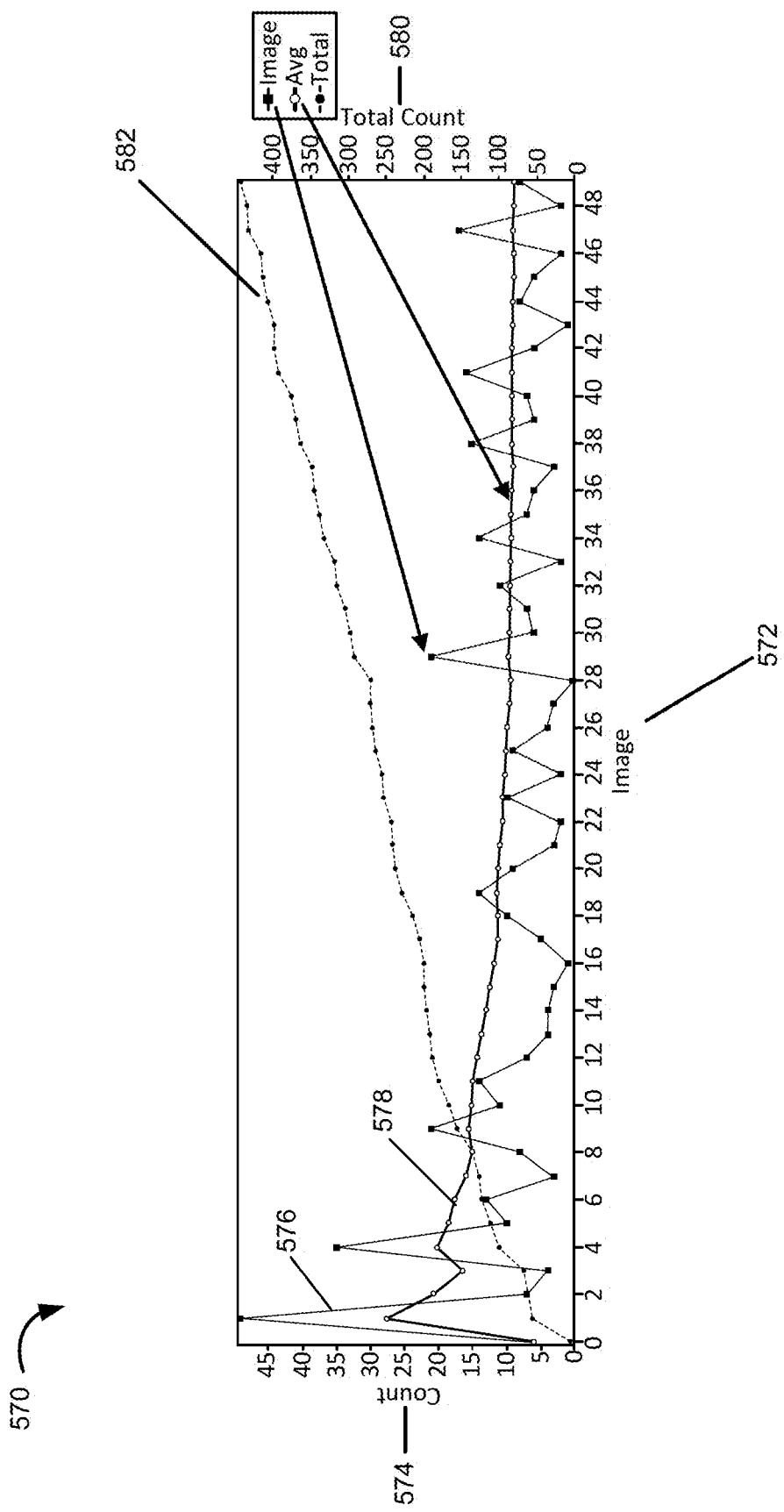
FIG. 23 illustrates a graphical display of white blood cell counts obtained during image analysis.

FIG. 23 schematically illustrates a graphical display 570 of the white blood cell counts obtained during image analysis. For example, the graphical display 570 is generated from data obtained during the image analysis performed by the computing device 116 described above in FIG. 22.

The x-axis 572 of the graphical display 570 can represent the number of images captured. For example, 50 images of the sample were captured by the optical system 404 (e.g., images 0 to 49). The first y-axis 574 on the left-hand side of the graphical display 570 represents a white blood cell count. A first line 576 represents the number of white bloods cells counted for each image. For example, 4 white blood cells were counted in the first image (e.g., image 0), 50 white blood cells were counted in the second image, 7 white blood cells were counted in the third image, 4 white blood cells were counted in the fourth image, 35 white blood cells were counted in the fifth image, and so on. A second line 578 represents an average number of white blood cells counted per image. Continuing with the example above, if 4 white blood cells are counted in the first image and 50 white blood cells are counted in the second image, then the average white blood cell count at the second image is an average of the count at the first and the second image, which is 27 (e.g., (4+50)/2). Similarly, the average white blood cell count at the third image is an average of the count at the first, second, and third image, which is about 20.

The second y-axis 580 on the right-hand side of the graphical display 570 represents a cumulative white blood cell count, and associated line 582 represents a cumulative white blood cell count at each image. For example, as the white blood cell count for a next image is determined, the white blood cell count is added to the previous count of white blood cells. Continuing with the example above, after the first image the total white blood cell count is 4, after the second image the total white blood cell count is 54, after the third image the total white blood cell count is 61, after the fourth image the total white blood cell count is 65, after the fifth image the total white blood cell count is 100, and so on. The value of the cumulative white blood cell count at the final image (e.g., image 49) is the total number of white blood cells in the plurality of images. Here, the total number of white blood cells in the plurality of images is about 442 white blood cells. The concentration of white blood cells in the specimen can then be estimated based on the total number of white blood cells in the plurality of images and a total aliquot volume in the plurality of images, which can determined as part of the image analysis by the computing device 116 as described in detail above in FIG. 22.

Although this graphical display 570 can be generated by the computing device 116, in some examples, the graphical display 570 is not provided externally to a user. For example, the graphical display 570 is not provided through a user interface of the touch display 122 of the sample preparation instrument 100. Instead, only a range in which the estimate of white blood cell concentration falls is displayed to the user through the user interface of the touch display 122 of the sample preparation instrument 100. In further examples, the sample volume of the specimen and/or an alert if a determination is made not to process the specimen based on the estimate may also be displayed.

Figure 24:
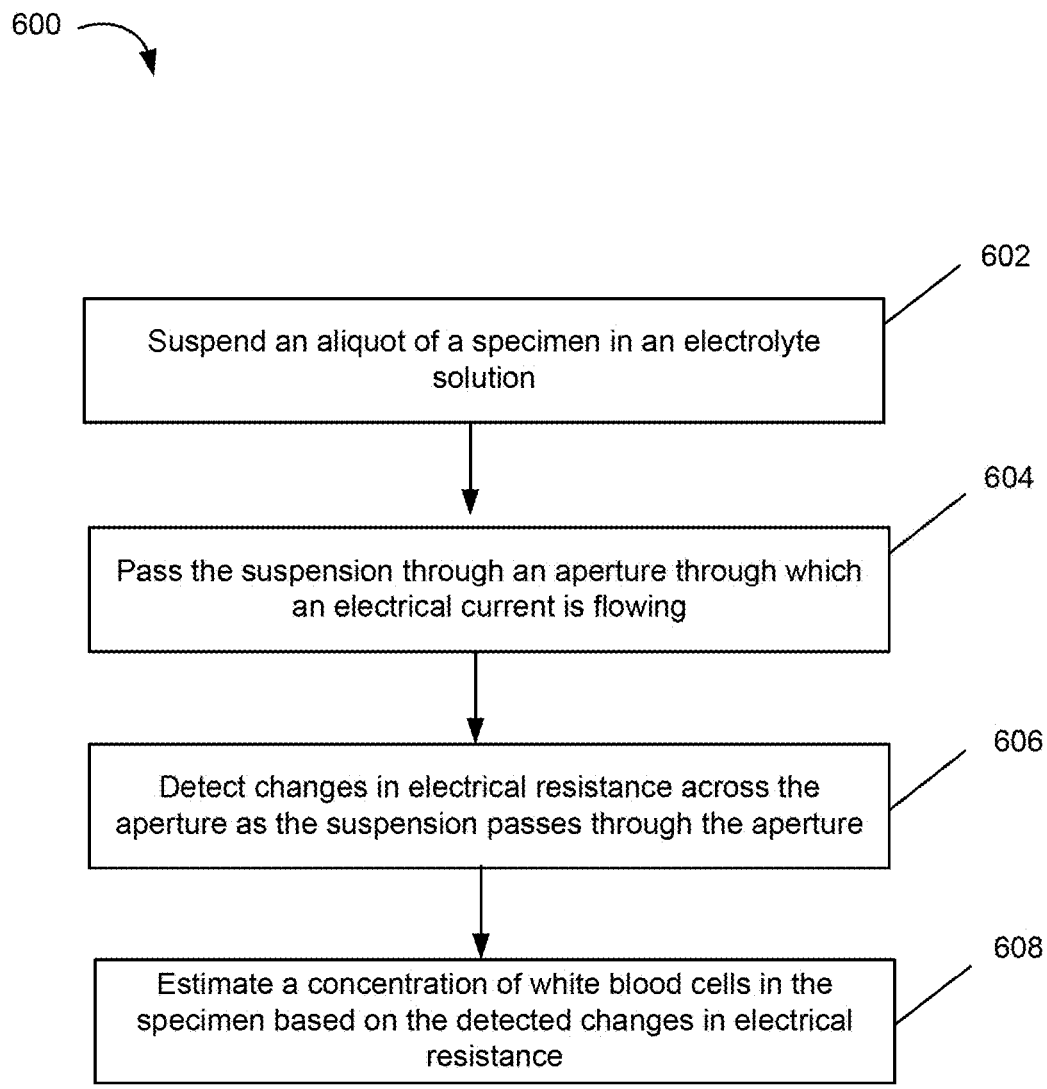
FIG. 24 is a flowchart illustrating an electrical resistance method for estimating a white blood cell concentration in a specimen.

FIG. 24 is a flowchart illustrating an electrical resistance method 600 for estimating a white blood cell concentration in a specimen. The method 600 can be performed by the cell concentration estimator 106 of the sample preparation instrument 100. However, the cell concentration estimator 106 can have different components than the cell concentration estimator 106 described in conjunction with the optical method 450 of estimation (e.g., different from the cell concentration estimator 106 described in FIGS. 16-23). For example, the electrical resistance method 600 employed can be the Coulter Principle, and the cell concentration estimator 106 is a counting bath that includes at least a first chamber and a second chamber comprising an electrolyte solution, an aperture connecting the first chamber to the second chamber, and at least two electrodes. The electrodes can be placed at each end of the aperture to create an electric field that is applied through the aperture (e.g., cause an electrical current to flow through the aperture). In some examples, the aperture is a channel.

At operation 602, an aliquot of the specimen is suspended in the electrolyte solution and dispensed into the first chamber of the counting bath. In some examples, the aliquot of the specimen can also be lysed and diluted within the counting bath. At operation 604, the suspension is passed through the aperture through which the electrical current is flowing. For example, the suspension is advanced from the first chamber to the second chamber through the aperture. In some examples, the cell concentration estimator 106 also includes a pump to advance the suspension from the first chamber to the second chamber. In other examples, the suspension flows from the first chamber to the second chamber as a result of differential pressure, for example. As the cells of the specimen within the suspension flow through the aperture, an electrical resistance across the aperture changes.

At operation 606, the changes in the electrical resistance are detected. A concentration of white blood cells in the aliquot, which is representative of the concentration of white blood cells in the specimen, can then be estimated at operation 608 based on the detected changes in the electrical resistance. In some examples, the electrical resistance changes are detected and measured electronically as a series of pulses. The pulses can then be processed and counted by the computing device 116, for example, in order to estimate the number of white blood cells per volume of the aliquot.

Figure 25:
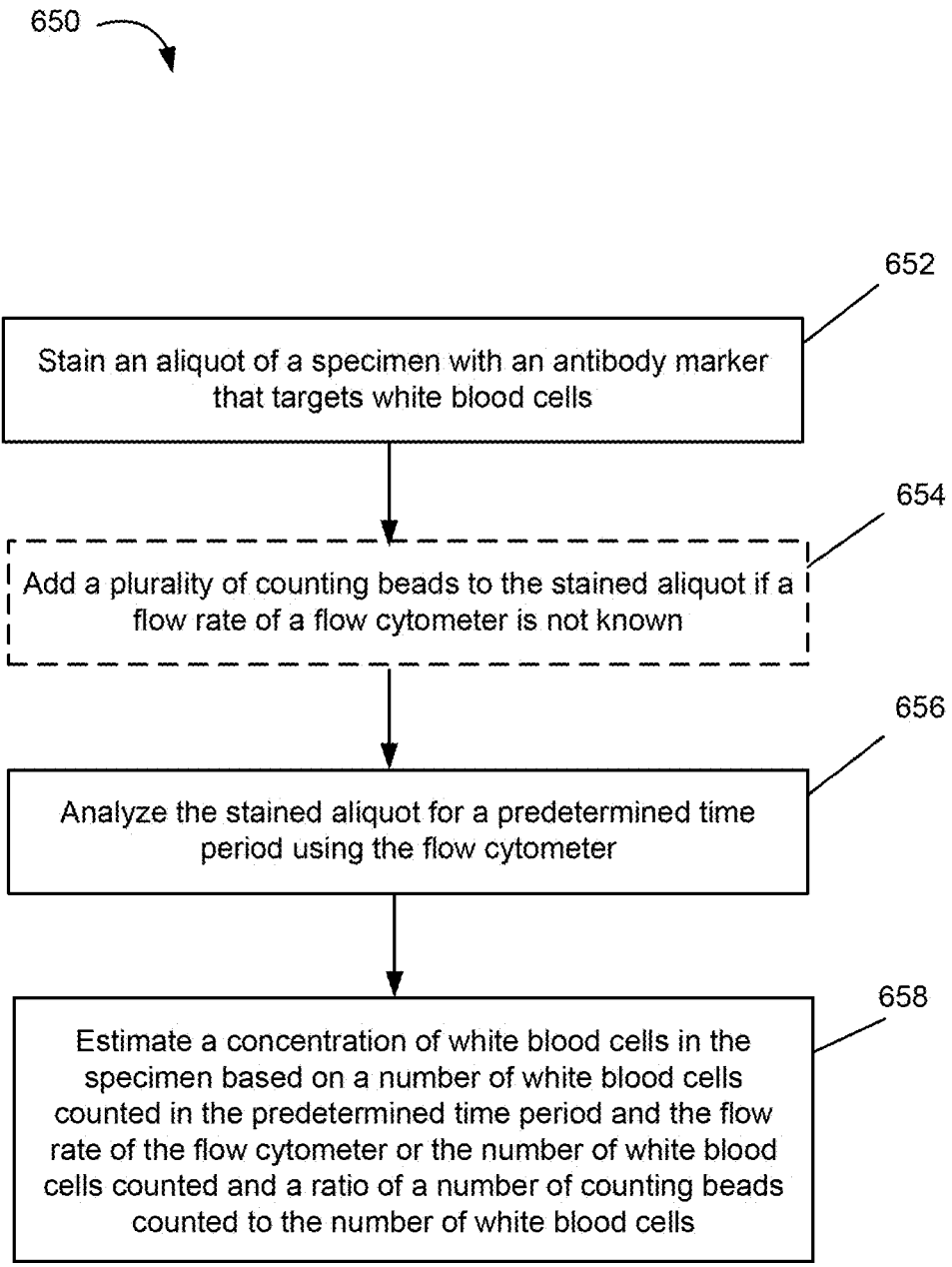
FIG. 25 is a flowchart illustrating a flow cytometry method for estimating a white blood cell concentration in a specimen.

FIG. 25 is a flowchart illustrating a flow cytometry method 650 for estimating a white blood cell concentration in a specimen. The method 650 can be performed by the cell concentration estimator 106 of the sample preparation instrument 100. However, the cell concentration estimator 106 can have different components than the cell concentration estimator 106 described in conjunction with the optical method 450 of estimation (e.g., different from the cell concentration estimator 106 described in FIGS. 16-23) and the cell concentration estimator 106 described in conjunction with the electrical resistance method 600 of estimation in FIG. 24. For example, the cell concentration estimator 106 can be a flow cytometer. In further examples, the method 650 can be performed by the sample preparation and analysis instrument 150, where the cell concentration estimator and the sample analyzer 152 can be a same component, such as a flow cytometer.

The method 650 begins at operation 652, where an aliquot of the specimen is stained with an antibody marker that targets white blood cells. In some examples, the aliquot of the specimen and antibody marker are incubated. Additionally, one or more lytic reagents can be added. If a flow rate of the flow cytometer is not known, a plurality of counting beads are also added to the stained aliquot of the specimen at optional operation 654 to provide a reference for determining a volume of the sample.

At operation 656, the stained aliquot of the specimen is analyzed for a predetermined time period using the flow cytometer. The analysis includes a count of white blood cells over the predetermined time period, the antibody marker enabling the white blood cells to be distinguishable from other cells in the sample. Additionally, if the counting beads were added at optional operation 654, the analysis can further include a count of counting beads.

At operation 658, the concentration of white blood cells in the aliquot, which is representative of the concentration of white blood cells in the specimen, is then estimated based on a number of white blood cells counted in the predetermined time period at operation 656 and the flow rate of the flow cytometer, if known. If the flow rate of the flow cytometer is not known, then the concentration of white blood cells in the specimen is estimated based on the number of white blood cells counted and a ratio of the number of counting beads counted at operation 656 to the number of white blood cells.

The various examples and teachings described above are provided by way of illustration only and should not be construed to limit the scope of the present disclosure. Those skilled in the art will readily recognize various modifications and changes that may be made without following the examples and applications illustrated and described herein, and without departing from the true spirit and scope of the present disclosure.

What is claimed is:

1. A sample preparation instrument comprising:
   an input station configured to receive a specimen including white blood cells;
   a cell concentration estimator configured to estimate a concentration of the white blood cells in the specimen;
   a transfer station configured to dispense a sample volume of the specimen, wherein the sample volume is based on the concentration of the white blood cells in the specimen estimated by the cell concentration estimator;
   a reagent station including a labeling reagent;
   a lysing station including a first lytic reagent;
   an output station configured to provide a sample following an addition of the labeling reagent to the sample volume by the transfer station and an addition of the first lytic reagent to the sample volume by the transfer station; and
   a computing device including a processing device and a memory coupled to the processing device, wherein the memory stores instructions that, when executed by the processing device, cause the processing device to enable further processing of the sample only when:
   the concentration of the white blood cells for the specimen estimated by the cell concentration estimator is above a predetermined minimum white blood cell concentration value; and
   the concentration of the white blood cells for the specimen estimated by the cell concentration estimator is below a predetermined maximum white blood cell concentration value wherein the predetermined maximum white blood concentration value is higher than the predetermined minimum white blood concentration value.

2. The sample preparation instrument according to claim 1, wherein the cell concentration estimator includes:
   a mixing chamber configured to receive an aliquot of the specimen;
   a counting chamber connected to the mixing chamber;
   a fluidic pump configured to advance a portion of the aliquot from the mixing chamber to the counting chamber; and
   an optical system configured to capture a plurality of images of the portion of the aliquot in the counting chamber.

3. The sample preparation instrument according to claim 2, wherein the mixing chamber comprises:
   a vessel having an open end;
   a cap positioned on the open end of the vessel, the cap comprising a plurality of input ports and an opening for a transfer station probe to dispense the aliquot into the vessel; and
   a motor for mixing the aliquot of the specimen with one or more reagents dispensed into the vessel via the plurality of input ports, wherein the one or more reagents include a second lytic reagent and a diluent reagent.

4. The sample preparation instrument according to claim 2, wherein the counting chamber comprises one or more transparent flow cells.

5. The sample preparation instrument according to claim 2, wherein the optical system includes a camera, a light source, and a lens.

6. The sample preparation instrument according to claim 1, wherein the cell concentration estimator includes an optical system and the memory stores instructions that, when executed by the processing device, cause the processing device to:
   receive a plurality of images of an aliquot of the specimen captured by the optical system;
   determine a total number of white blood cells in the plurality of images based on a number of white blood cells counted in each image;
   determine a total volume of the aliquot in the plurality of images; and
   estimate the concentration of white blood cells based on the total number of white blood cells and the total volume of the aliquot in the plurality of images.

7. The sample preparation instrument according to claim 1, wherein the memory stores instructions that, when executed by the processing device, cause the processing device to:
   receive a selection of a panel to perform;
   retrieve, from the memory, a set of predefined rules for preparing the specimen for the panel, the set of predefined rules including volumes of the sample corresponding to one or more ranges of white blood cell concentrations; and
   based on the set of predefined rules and the concentration of white blood cells in the specimen estimated by the cell concentration estimator determine the sample volume.

8. The sample preparation instrument according to claim 7, wherein the set of predefined rules further include the predetermined minimum white blood cell concentration value and the predetermined maximum white blood concentration value, and the one or more ranges of white blood cell concentrations are between the predetermined minimum white blood cell concentration value and the predetermined maximum white blood cell concentration value.

9. The sample preparation instrument according to claim 1, further comprising a display configured to provide a user interface including one or more of:
   a range into which the concentration of white blood cells estimated by the cell concentration estimator falls, the sample volume, and an alert when further processing of the sample is is not enabled.

10. The sample preparation instrument according to claim 1, wherein the cell concentration estimator includes:
   a first chamber configured to receive an aliquot of the specimen suspended in an electrolyte solution;
   a second chamber;
   an aperture connecting the first chamber to the second chamber and through which the aliquot of the specimen suspended in the electrolyte solution can flow from the first chamber to the second chamber; and at least two electrodes configured to create an electric field within the cell concentration estimator, wherein the concentration of white blood cells in the specimen estimated by the cell concentration estimator is determined based on detected changes in electrical resistance across the aperture as the aliquot of the specimen flows through the aperture.

11. The sample preparation instrument according to claim 1, wherein the sample preparation instrument has an attachment and the cell concentration estimator is detachably attached to the attachment.

12. A sample preparation and analysis instrument comprising:

an input station configured to receive a specimen having white blood cells;

a cell concentration estimator configured to estimate a concentration of the white blood cells in the specimen;

a transfer station configured to dispense a sample volume of the specimen, wherein the sample volume is based on the concentration of white blood cells in the specimen estimated by the cell concentration estimator;

a reagent station including a labeling reagent;

a lysing station including a lytic reagent;

a sample analyzer configured to perform an analysis on the sample volume following an addition of the labeling reagent to the sample volume and an addition of the lytic reagent to the sample volume;

an output station configured to output results of the analysis; and a computing device including a processing device and a memory coupled to the processing device, wherein the memory stores instructions that, when executed by the processing device, cause the processing device to enable a processing of the sample only when:

the concentration of the white blood cells for the specimen estimated by the cell concentration estimator is below a predetermined maximum white blood cell concentration value wherein the predetermined maximum white blood concentration value is higher than a predetermined minimum white blood concentration value.

* * * * *